(12) United States Patent
Bawendi et al.

(10) Patent No.: US 11,077,213 B2
(45) Date of Patent: Aug. 3, 2021

(54) SHORT-WAVELENGTH INFRARED (SWIR) FLUORESCENCE IN VIVO AND INTRAVITAL IMAGING WITH SEMICONDUCTOR NANOCRYSTALS

(71) Applicant: MASSACHUSETTS INSTITUTE OF TECHNOLOGY, Cambridge, MA (US)

(72) Inventors: Moungi G. Bawendi, Cambridge, MA (US); Daniel K. Harris, Wilton, CT (US); Oliver T. Bruns, Boston, MA (US); Thomas S. Bischof, Medford, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 367 days.

(21) Appl. No.: 14/258,681

(22) Filed: Apr. 22, 2014

(65) Prior Publication Data

US 2015/0273085 A1    Oct. 1, 2015

Related U.S. Application Data

(60) Provisional application No. 61/814,528, filed on Apr. 22, 2013.

(51) Int. Cl.
*A61B 5/00* (2006.01)
*A61K 49/00* (2006.01)
*C30B 29/40* (2006.01)
*C09K 11/74* (2006.01)
(Continued)

(52) U.S. Cl.
CPC ........ *A61K 49/0067* (2013.01); *A61B 5/0062* (2013.01); *A61B 5/0071* (2013.01);
(Continued)

(58) Field of Classification Search
CPC . C09K 11/565; C09K 11/7492; C09K 11/883; C30B 7/14; C30B 29/40;
(Continued)

(56) References Cited

U.S. PATENT DOCUMENTS 6,319,426 B1 * 11/2001 Bawendi ............... B82Y 15/00
252/301
7,181,266 B2    2/2007 Frangioni et al.
(Continued)

FOREIGN PATENT DOCUMENTS

WO    2012092195 A1    7/2012

OTHER PUBLICATIONS

International Search Report and Written Opinion dated Mar. 23, 2015 in PCT/US14/34988 (12 pages).
(Continued)

*Primary Examiner* — Elmer M Chao
(74) *Attorney, Agent, or Firm* — Honigman LLP

(57) ABSTRACT

InAs based core-shell particles which leads to tunable, narrow emitting semiconductor nanocrystals with a very high quantum yield which can be preserved in physiological buffers with long stability can used for short wavelength infrared (SWIR) imaging. Increased resolution with reduced read time and increased imaging frequency can provide advantages in in vivo applications.

13 Claims, 42 Drawing Sheets

(51) Int. Cl.
  *C09K 11/56* (2006.01)
  *C30B 7/14* (2006.01)
  *C30B 29/60* (2006.01)
  *C09K 11/88* (2006.01)
  *A61B 5/02* (2006.01)

(52) U.S. Cl.
  CPC ........ *A61B 5/0084* (2013.01); *A61B 5/02007* (2013.01); *A61B 5/489* (2013.01); *C09K 11/565* (2013.01); *C09K 11/7492* (2013.01); *C09K 11/883* (2013.01); *C30B 7/14* (2013.01); *C30B 29/40* (2013.01); *C30B 29/60* (2013.01); *Y10S 977/773* (2013.01); *Y10S 977/83* (2013.01)

(58) Field of Classification Search
  CPC .... C30B 29/60; Y10S 977/773; Y10S 977/83; A61B 5/0062; A61B 5/02007; A61B 5/489; A61B 5/0084; A61B 5/0071; A61K 49/0067
  See application file for complete search history.

(56) References Cited

U.S. PATENT DOCUMENTS

| | | | |
|---|---|---|---|
| 2006/0157720 A1* | 7/2006 | Bawendi | C09K 11/565 257/98 |
| 2010/0183504 A1 | 7/2010 | Chen | |
| 2011/0223110 A1* | 9/2011 | Bartel | B82Y 5/00 424/9.6 |
| 2012/0056289 A1 | 3/2012 | Tian et al. | |
| 2013/0009129 A1 | 1/2013 | Sargent et al. | |
| 2014/0001436 A1* | 1/2014 | Welch | B82Y 30/00 257/14 |

OTHER PUBLICATIONS

International Preliminary Report on Patentability dated Nov. 5, 2015 in PCT/US14/34988 (8 pages).

* cited by examiner (d)

(e)

(f)

(g)

SHORT-WAVELENGTH INFRARED (SWIR) FLUORESCENCE IN VIVO AND INTRAVITAL IMAGING WITH SEMICONDUCTOR NANOCRYSTALS

CLAIM OF PRIORITY

This application claims priority to U.S. Application No. 61/814,528, filed Apr. 22, 2013, which is incorporated by reference in its entirety.

FEDERALLY SPONSORED RESEARCH OR DEVELOPMENT

This invention was made with government support under Grant Nos. CA126642 and EB015871 and CA151884 awarded by the National Institutes of Health and under Grant No. DGE1122374 awarded by the National Science Foundation and under Contract No. W911NF-13-D-0001 awarded by the Army Research Office. The government has certain rights in the invention.

TECHNICAL FIELD

The invention relates to imaging tissue and organs.

BACKGROUND

Semiconductor nanocrystals having small dimensions can have properties intermediate between molecular and bulk forms of matter. For example, nanocrystals of semiconductor materials having sufficiently small dimensions can exhibit quantum confinement of excitons (excited state electron-hole pair) in all three dimensions. Quantum confinement leads to an increase in the effective band gap of the material with decreasing crystallite size. Consequently, both the optical absorption and emission of nanocrystals shift to the blue (i.e., to higher energies) as the size of the nanocrystal decreases. Semiconductor nanocrystals can have a narrow fluorescence band whose emission wavelength is tunable with the size and material of the nanocrystals.

The quantum efficiency of emission from nanocrystals having a core of a first semiconductor material can be enhanced by applying an overcoating of a second semiconductor material such that the conduction band of the second semiconductor material is of higher energy than that of the first semiconductor material, and the valence band of the second semiconductor material is of lower energy than that of the first semiconductor material. As a result, both charge carriers of an exciton, i.e., electrons and holes, are confined in the core of the nanocrystal.

SUMMARY

A method of imaging can include introducing a composition including a particle containing a semiconductor nanocrystal into a subject, exciting the particle with an excitation light source, detecting emission from the particle in short wavelength infrared (SWIR) spectrum, and generating a real-time image of an area surrounding of the subject from the detected SWIR emission. The excitation spectrum can be tunable. Detecting the emission can include sampling at an imaging frequency of at least 6 fps, at least 20 fps, at least 30 fps, at least 40 fps, or at least 48 fps.

In certain embodiments, the semiconductor nanocrystal can include a core of a first semiconductor material and an overcoating of a second semiconductor material on the core wherein the first semiconductor material and the second semiconductor material are selected so that, upon excitation, one carrier is substantially confined to the core and the other carrier is substantially confined to the overcoating. Specifically, the semiconductor nanocrystals can be an InAs-based core-shell particle. A quantum yield of the semiconductor nanocrystal can be at least 1%, at least 10%, at least 20%, or at least at least 30%.

In certain embodiments, the semiconductor nanocrystal can emit light having a wavelength greater than 900 nm, great than 1000 nm, great than 1100 nm, great than 1200 nm, great than 1300 nm, great than 1400 nm, great than 1500 nm, great than 1600 nm, or great than 1700 nm. A hydrodynamic diameter of the semiconductor nanocrystal is less than 30 nm.

An imaging composition can include a semiconductor nanocrystal including a core and an outer layer including a solubilizing ligand, where the nanocrystal emits light in short wavelength infrared (SWIR) spectrum and a biocompatible carrier compatible with the solubilizing ligand. The imaging composition can include a lipid, such as a PEG related lipid.

The nanocrystal can be highly luminescent, monodisperse, photostable, and with appropriate surface derivitization water-soluble and biocompatible. Nanocrystal can have ligands that can be copolymers, where the different monomer components are each selected to confer a desired property to the derivitazed nanocrystals. The resulting nanocrystals can be of small size, highly stable (both over time and over a wide pH range), can have a high quantum yield, can be easily derivatized by further chemical modification of the ligands, and can have a low level of non-specific binding to biological structures (e.g., cell surfaces, tissues, proteins, nucleic acids, etc.).

In one aspect, a nanomaterial can include a nanocrystal, and an outer layer including a ligand. The ligand can include a first monomer unit including a first moiety having affinity for a surface of the nanocrystal, a second monomer unit including a second moiety having a high water solubility, and a third monomer unit including a third moiety having a selectively reactive functional group or a selectively binding functional group.

In certain embodiments, the first monomer unit, the second monomer unit, and the third monomer unit can be each different from one another. The ligand can a polymer having a plurality of monomer units, the plurality including the first monomer unit, the second monomer unit, and the third monomer unit. The ligand can be a random copolymer including the first monomer unit, the second monomer unit, and the third monomer unit. The ligand can be a random copolymer consisting essentially of the first monomer unit, the second monomer unit, and the third monomer unit.

The first moiety can be an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, an aromatic amine moiety, or a combination thereof.

The ligand can include a polymer including a random copolymer including regions having each of the following formulae:

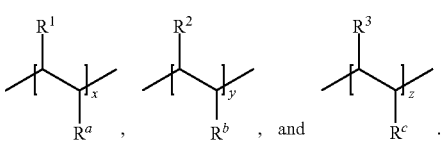

In the copolymer, $R^1$ can be a first moiety having affinity for a surface of the nanocrystal, $R^2$ can be a second moiety having a high water solubility, $R^3$ can be a third moiety having a selectively reactive functional group or a selectively binding functional group, each of $R^a$, $R^b$, and $R^c$, independently, can be substituted or unsubstituted alkyl, substituted or unsubstituted alkoxy, substituted or unsubstituted aryl, or substituted or unsubstituted aryloxy, and each of x, y, and z, independently, a positive integer.

In the copolymer, $x/(x+y+z)$ can be in the range of 0.1 to 0.9, $y/(x+y+z)$ can be in the range of 0.05 to 0.75, and $z/(x+y+z)$ can be in the range of 0.005 to 0.25.

A region of the formula can have of formula (I):

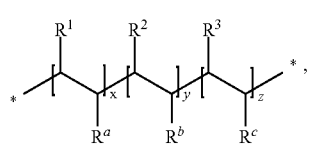

(I)

wherein each of x, y, and z, independently, is an integer selected from group consisting of 1, 2, 3, 4, 5, 6, 7, 8, 9 and 10.

In the ligand, $R^1$ can have the formula $-L^1-T^1$, wherein $L^1$ can be a bond or an alkylene, alkenylene, or arylene linking group having 1 to 8 chain atoms and can be optionally interrupted or terminated by —O—, —S—, —NR$^4$—, —CO—, or a combination thereof, $T^1$ can be an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, an aromatic amine moiety, or a combination thereof, and $R^4$ can be hydrogen, hydroxy, alkyl, haloalkyl, alkenyl, alkynyl, cycloalkyl, cycloalkenyl, or aryl.

In the ligand, $R^2$ can have the formula $-L^2-T^2$, wherein $L^2$ can be a bond or an alkylene, alkenylene, or arylene linking group having 1 to 8 chain atoms and can be optionally interrupted or terminated by —O—, —S—, —NR$^4$—, —CO—, or a combination thereof; $T^2$ can be —[O—CH$_2$—CHR$^5$]$_n$—R$^6$ wherein $R^5$ can be H or $C_1$ to $C_3$ alkyl, and $R^6$ can be H, —OH, $C_1$ to $C_6$ alkyl, $C_1$ to $C_6$ alkoxy, aryl, aryloxy, arylalkyl, or arylalkoxy, and n can be an integer in the range of 0 to 30, and $R^4$ can be hydrogen, hydroxy, alkyl, haloalkyl, alkenyl, alkynyl, cycloalkyl, cycloalkenyl, or aryl.

In the ligand, $R^3$ can have the formula $-L^3-T^3$, wherein $L^3$ can be a bond or an alkylene, alkenylene, or arylene linking group having 1 to 8 chain atoms and can be optionally interrupted or terminated by —O—, —S—, —NR$^4$—, —CO—, or a combination thereof, $T^3$ can be —[O—CH$_2$—CHR$^7$]$_m$—R$^8$ wherein $R^7$ can be H or $C_1$ to $C_3$ alkyl, and $R^8$ can be $C_1$ to $C_6$ aminoalkyl or $C_1$ to $C_6$ azidoalkyl, and m can be an integer in the range of 0 to 30, and $R^4$ can be hydrogen, hydroxy, alkyl, haloalkyl, alkenyl, alkynyl, cycloalkyl, cycloalkenyl, or aryl.

In the ligand, $R^1$ can have the formula $-L^1-T^1$, wherein $L^1$ can be a bond or an alkylene, alkenylene, or arylene linking group having 1 to 8 chain atoms and can be optionally interrupted or terminated by —O—, —S—, —NR$^4$—, —CO—, or a combination thereof, $T^1$ can be an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, an aromatic amine moiety, or a combination thereof. $R^2$ can have the formula $-L^2-T^2$, wherein $L^2$ can be a bond or an alkylene, alkenylene, or arylene linking group having 1 to 8 chain atoms and can be optionally interrupted or terminated by —O—, —S—, —NR$^4$—, —CO—, or a combination thereof, $T^2$ can be —[O—CH$_2$—CHR$^5$]$_n$—R$^6$ wherein $R^5$ can be H or $C_1$ to $C_3$ alkyl, and $R^6$ can be H, —OH, $C_1$ to $C_6$ alkyl, $C_1$ to $C_6$ alkoxy, aryl, aryloxy, arylalkyl, or arylalkoxy, and n can be an integer in the range of 0 to 30. And, $R^3$ can have the formula $-L^3-T^3$, wherein $L^3$ can be a bond or an alkylene, alkenylene, or arylene linking group having 1 to 8 chain atoms and can be optionally interrupted or terminated by —O—, —S—, —NR$^4$—, —CO—, or a combination thereof, $T^3$ can be —[O—CH$_2$—CHR$^7$]$_m$—R$^8$ wherein $R^7$ can be H or $C_1$ to $C_3$ alkyl; and $R^8$ can be $C_1$ to $C_6$ aminoalkyl or $C_1$ to $C_6$ azidoalkyl, and m can be an integer in the range of 0 to 30, and each $R^4$, independently, can be hydrogen, hydroxy, alkyl, haloalkyl, alkenyl, alkynyl, cycloalkyl, cycloalkenyl, or aryl.

In the ligand, $L^1$, $L^2$, and $L^3$ can be each independently —C(O)NH—(CH$_2$)$_i$— wherein i is an integer in the range of 0 to 6. $T^1$ can be an imidazolyl moiety. $T^2$ can be —[O—CH$_2$—CH$_2$]$_n$—OR$^6$ wherein n can be an integer in the range of 5 to 25 and $R^6$ can be H, methyl, or ethyl. $T^3$ can be —[O—CH$_2$—CH$_2$]$_m$—R$^8$ wherein $R^8$ is $C_1$ to $C_6$ aminoalkyl or $C_1$ to $C_6$ azidoalkyl, and m can be an integer in the range of 0 to 10.

The nanocrystal can be a semiconductor nanocrystal, semiconductor material, a ceramic material, a magnetic material, or a metallic material.

In another aspect, an aqueous nanomaterial suspension can include the nanomaterial described above, wherein the aqueous nanocrystal suspension can remain stable as an aqueous suspension when stored under ambient conditions for at least 2 months.

In another aspect, a method of making a ligand can include mixing a first monomer or oligomer including a first moiety having affinity for a surface of the nanocrystal, a second monomer or oligomer including a second moiety having a high water solubility, and a third monomer or oligomer including a third moiety having a selectively reactive functional group or a selectively binding functional group, and forming a ligand from the first monomer or oligomer, the second monomer or oligomer, and the third monomer oligomer.

In another aspect, a method of making a nanomaterial can include contacting the ligand with a nanocrystal.

In another aspect, a ligand can include a polymer including a random copolymer including regions having each of the following formulae:

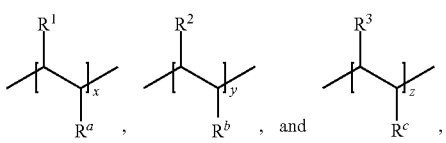

wherein R¹ is a first moiety having affinity for a surface of the nanocrystal, $R^2$ is a second moiety having a high water solubility, $R^3$ is a third moiety having a selectively reactive functional group or a selectively binding functional group, each of $R^a$, $R^b$, and $R^c$, independently, is substituted or unsubstituted alkyl, substituted or unsubstituted alkoxy, substituted or unsubstituted aryl, or substituted or unsubstituted aryloxy, and each of x, y, and z, independently, a positive integer.

An imaging apparatus can include a source of excitation light configured to direct the excitation light at a subject stage, a detector configured to collect emitted light from a subject on the subject stage; and an image generator configured to create a real-time image from the detected emitted light. In certain embodiments, the detector can sample at a frame rate at least 6 fps, at least 20 fps, at least 30 fps, at least 40 fps, or at least 48 fps. At emitted light is from a semiconductor nanocrystal having a quantum yield of at least 1%, at least 10%, at least 20%, or at least 30%.

Other features, objects, and advantages of the invention will be apparent from the description and drawings, and from the claims.

BRIEF DESCRIPTION OF THE DRAWINGS

FIGS. 11A-11D are photographs depicting a correlation of OFDI and (FIGS. 11A and 11C) and SWIR (FIGS. 11B and 11D).

DETAILED DESCRIPTION

Figure 1:
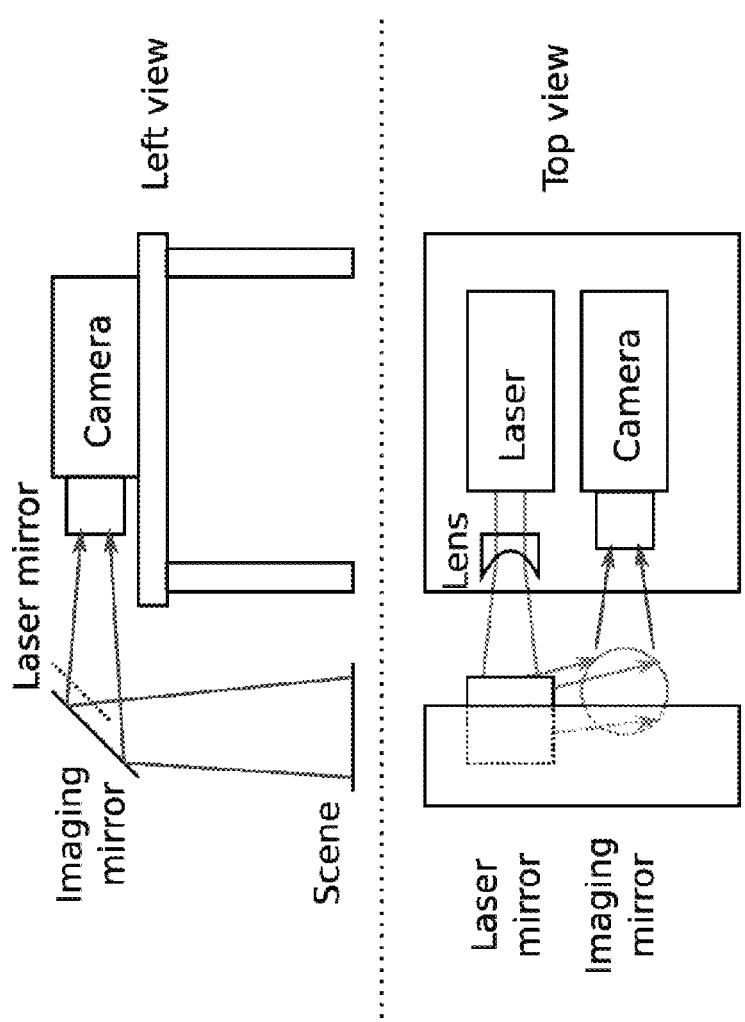
FIG. 1 depicts a schematic of the imaging apparatus.

Optical imaging is cheaper and easier to perform compared to other techniques like ultrasound, MRI or computed tomography in small animals. The optimum of tissue penetration is reached by light wavelengths between 1000 and 1700 nm, which belongs to short wavelength infrared (SWIR) region. See Lim, Y. T. et al. Selection of semiconductor nanocrystals wavelengths for biomedical assays and imaging. *Molecular imaging* 2, 50-64 (2003), which is incorporated by reference in its entirety. But this region was not readily available for imaging so far due to missing detection and labeling technology. Typically in the SWIR imaging technology, SWIR region is referred to as wavelengths of 1000 nm~3000 nm. In some circumstances, materials that emit between 750 nm and 1400 nm can have particular applications. In other circumstances, materials that emit between 1400 nm to 3000 nm can have particular applications. To detect emission in the SWIR region, a non-silicon based detector, for example indium or gallium semiconductor based, (e.g. InGaAs) can be used for the imaging technology described herein.

Recently other groups demonstrated in vivo fluorescence imaging in this region with single walled carbon nanotubes (SWCNTs) as well as non-tunable AgS semiconductor nanocrystals. See Lim, Y. T. et al. Selection of quantum dot wavelengths for biomedical assays and imaging. *Molecular imaging* 2, 50-64 (2003), Hong, G. et al. Multifunctional in vivo vascular imaging using near-infrared II fluorescence. *Nature Medicine* 18, 1841-6 (2012), Yi, H. et al. M13 phage-functionalized single-walled carbon nanotubes as nanoprobes for second near-infrared window fluorescence imaging of targeted tumors. *Nano letters* 12, 1176-83 (2012), Hong, G. et al. In Vivo fluorescence imaging with ag(2) s quantum dots in the second near-infrared region. *Angewandte Chemie (International ed. in English)* 51, 9818-21 (2012) and Zhang, Y. et al. Ag2S quantum dot: a bright and biocompatible fluorescent nanoprobe in the second near-infrared window. *ACS nano* 6, 3695-702 (2012), each of which is incorporated by reference in its entirety. It has been shown that SWIR imaging is performing better than near infrared imaging, ultrasound and micro computed tomography.

Synthesis schemes for InAs based core-shell particles which leads to tunable, narrow emitting semiconductor nanocrystals with a very high quantum yield which can be preserved in physiological buffers used for in vivo application were developed. For related technology, see Harris, D. K. & Bawendi, M. G. Improved precursor chemistry for the synthesis of III-V quantum dots. *Journal of the American Chemical Society* 134, 20211-3 (2012), which is incorporated by reference in its entirety.

In contrast to single walled carbon nanotubes, semiconductor nanocrystals have a quantum yield which is two orders of magnitude higher (0.3% vs. 30%). Additionally InAs based core-shell particles exhibit narrow emission spectra, whereas SWCNTs which have a broad emission spectrum. The emission spectrum of InAs based core-shell particles can be tuned between 900 nm and 1500 nm allowing multiplexing with multiple different semiconductor nanocrystals in the SWIR region. This is not possible with either SWCNTs or AgS semiconductor nanocrystals. Also, the excitation spectrum of InAs based core-shell particles is tunable and broad. In contrast to SWCNTs and AgS semiconductor nanocrystals, InAs based core-shell particles can be excited at 800 nm and longer wavelengths. This improves the tissue penetration for fluorescence imaging dramatically. In addition, after transfer into aqueous buffers they still exhibit a high quantum yield of up to 30% and are stable over long storage times on the shelf (at least 9 months). The hydrodynamic diameter of InAs based core-shell particles in water is much smaller than SWCNTs (25 nm spherical vs. 500 nm and longer rod shaped SWCNTs).

Two imaging setups which perform much better than the published state of the art were developed. The first is macro imaging setup and the second a microscope. The resolution of the disclosed setup can be 4 times the number of pixels (256×320 vs. 512×640), and the read time can be reduced to less than less than 80 ms, less than 70 ms, less than 60 ms, less than 50 ms, less than 40 ms, less than 30 ms, less than 20 ms, or less than 10 ms. This allows to increase the imaging frequency to at least 6 fps, at least 20 fps, at least 30 fps, at least 40 fps, or at least 48 fps. The sensitivity range can be controlled and ranges now from 950 nm to 1700 nm compared to 950 nm to 1620 nm, which allows to detect one additional color when multiplexing.

By combining InAs based core-shell particles for use with the imaging setups, many novel applications are demonstrated, especially in the field of in vivo animal imaging. Due to the much higher quantum yield of InAs based core-shell particles, two orders of magnitude higher signal can be generated. This can be utilized in many ways. One is high frame rate imaging with 48 fps or higher, which allows to resolve fast motions. For example, the heart beat in a mouse can be visualized in a non-invasive and contact-free way. Previous setups and labels were not fast enough for this. Also, vital signs like heart rate and breathing rate in awake and behaving mice can be visualized and detected without anesthesia or constraining of the mouse. The fast motion of the actively behaving mouse is resolved without distortion by the disclosed imaging approach. In the disclosed microscope setting, the hemodynamics of blood flowing through different organs like liver or brain can be resolved without being distorted by motion artifacts. The rhythmic changes in the blood caused by the fast pumping cycle of the heart can also be resolved. With the microscope, one can reach as deep as two-photon microscopy but image with a much higher frame rate (~4 fps@512×512 vs. 50 fps@ 620×512). At the same time, a much better signal to noise ratio and increased dynamic range can be demonstrated.

Due to the tunability and higher quantum yield of InAs based core-shell particles, multiple 'colors' in the SWIR region can be detected. This can be utilized in many ways. One is multiplexing or 'color' SWIR imaging. For example, 5 and more different 'colors' of semiconductor nanocrystals can be imaged. Imaging with at least 2 different colors in living mice is demonstrated. More colors are possible. Background free video rate imaging in a living mouse with a second semiconductor nanocrystals color is demonstrated after the first semiconductor nanocrystals solution was already injected. In contrast to the published applications demonstrated by other groups with SWCNTs and AgS, InAs based core-shell particles have not only more signal but also much better capabilities for functionalizing and targeting. Functionalization with human lipid compositions for imaging of energy metabolism and formulation of small pegylated semiconductor nanocrystals for functional liver imaging was already demonstrated.

These technical developments can be applied for many different biomedical problems like heart disease, liver disease, immunologic disorders and cancer. The combination of InAs based core-shell particles and new detection technology has the potential to dramatically improve all current applications fluorescence based approaches in general. Some applications of SWIR imaging technology with novel semiconductor nanocrystals include macro imaging/whole body imaging. For example, the disclosed SWIR imaging can be applied to perfusion imaging of heart or brain, optical angiography (e.g. microvascular perfusion), contact free optical cardiography, contact free optical monitoring vital signs (breathing, heartbeat, movement of bowels) at high speed (e.g. 48 fps) in awake and behaving animals (e.g. nude mice), imaging of energy metabolism (e.g. heart, brown adipose tissue, liver, spleen), imaging of liver function (bile excretion of semiconductor nanocrystals), and semiconductor nanocrystals as contrast agents for different application routes (intravenous, intra peritoneal, subcutaneous, etc.). Also, the disclosed SWIR imaging technology can be applied to multiplexing with different semiconductor nanocrystals, for example, "multi-color" IR/SWIR imaging, high specific brightness (narrow emission with high quantum yield), and small size in comparison to CNTs. The disclosed SWIR imaging technology can be applied to microscopic imaging/intravital imaging, for example, measuring hemodynamics in vivo (such as tracking various cells in the blood stream) at high speed and increased depth, and fast measurement of vessel architecture and flow at the same time.

Semiconductor nanocrystals are a powerful class of fluorophores exhibiting high quantum yields, large molar extinction coefficients, exceptional photo-stability, and tunable emission wavelengths across the visible and near-IR spectral window. See, Dabbousi, B. O.; Rodriguez-Viejo, J.; Mikulec, F. V.; Heine, J. R.; Mattoussi, H.; Ober, R.; Jensen, K. F.; Bawendi, M. G., (CdSe)ZnS Core-Shell Quantum Dots: Synthesis and Characterization of a Size Series of Highly Luminescent Nanocrystallites. *J. Phys. Chem. B* 1997, 101, (46), 9463-9475, Zimmer, J. P.; Kim, S.-W.; Ohnishi, S.; Tanaka, E.; Frangioni, J. V.; Bawendi, M. G., Size Series of Small Indium Arsenide-Zinc Selenide Core-Shell Nanocrystals and Their Application to In Vivo Imaging. *J. Am. Chem. Soc.* 2006, 128, (8), 2526-2527, Bruchez, M., Jr.; Moronne, M.; Gin, P.; Weiss, S.; Alivisatos, A. P., Semiconductor nanocrystalsas Fluorescent Biological Labels. *Science* 1998, 281, (5385), 201, and Peng, Z. A.; Peng, X., Formation of High-Quality CdTe, CdSe, and CdS Nanocrystals Using CdO as Precursor. *J. Am. Chem. Soc.* 2001, 123, (1), 183-184, each of which is incorporated by reference in its entirety.

These properties make semiconductor nanocrystalsattractive candidates as biological fluorescent tags, especially since their exceptional brightness and stability enables single molecule tracking over extended periods of time. See Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S., Quantum Dots for Live Cells, in Vivo Imaging, and Diagnostics. *Science* 2005, 307, (5709), 538-544, Ballou, B.; Lagerholm, B. C.; Ernst, L. A.; Bruchez, M. P.; Waggoner, A. S., Noninvasive Imaging of Quantum Dots in Mice. *Bioconjug. Chem.* 2004, 15, (1), 79-86, Dahan, M.; Levi, S.; Luccardini, C.; Rostaing, P.; Riveau, B.; Triller, A., Diffusion Dynamics of Glycine Receptors Revealed by Single-Quantum Dot Tracking. *Science* 2003, 302, (5644), 442-445, Michaluk, P.; Mikasova, L.; Groc, L.; Frischknecht, R.; Choquet, D.; Kaczmarek, L., Matrix Metalloproteinase-9 Controls NMDA Receptor Surface Diffusion through Integrin beta 1 Signaling. *Journal of Neuroscience* 2009, 29, (18), 6007-6012, and Iyer, G.; Michalet, X.; Chang, Y. P.; Pinaud, F. F.; Matyas, S. E.; Payne, G.; Weiss, S., High Affinity scFv-Hapten Pair as a Tool for Quantum Dot Labeling and Tracking of Single Proteins in Live Cells. *Nano Letters* 2008, 8, (12), 4618-4623, each of which is incorporated by reference in its entirety. However, a major barrier towards the wide-spread use of semiconductor nanocrystals in these applications has been the difficulty in simultaneously optimizing five desirable nanocrystal properties for fluorescence labeling in live-cells: small size, high stability (both over time and in a wide pH range), high quantum yield, facile derivatizabilty, and low non-specific binding.

The nanocrystal can be a member of a population of nanocrystals having a narrow size distribution. The nanocrystal can be a sphere, rod, disk, or other shape. The nanocrystal can include a first semiconductor material, a ceramic material, a magnetic material, or a metallic material, for example, gold, iron oxide, titanium dioxide, cerium oxide or other metal chalcogenide or pnictide. The nanocrystal can include a first semiconductor material having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof. The first semiconductor material can include a Group II-VI compound, a Group II-V compound, a Group III-VI compound, a Group III-V compound, a Group IV-VI compound, a Group I-III-VI compound, a Group II-IV-VI compound, a Group II-IV-V compound, or mixtures thereof. For example, the first semiconductor material can include for example, ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof.

In some embodiments, the nanocrystal includes a first semiconductor material including a Group I-III-VI compound. For example, the first semiconductor material can include for example, a copper indium diselenide such as a doped copper indium diselenide or other copper indium diselenide, or alloyed copper indium diselenide, such as, for example, copper indium zinc diselenide, or copper indium gallium diselenide. The first semiconductor material can include a copper indium disulfide such as a doped copper indium disulfide or other copper indium disulfide, or alloyed copper indium disulfide. Other elements alloyed with copper indium diselenide and/or copper indium disulfide can include sulfur, aluminum, or silver; for example, $CuInS_2$, $CuIn(S, Se)_2$, $Cu(In, Al)Se_2$, $Cu(In, Ag)Se_2$, or others.

The nanocrystal can include a second semiconductor material. The second semiconductor material can a composition different from the composition of the first semiconductor material. The first and second semiconductor materials can be selected to provide a desired band structure, such as a type I or a type II heterostructure. The second semiconductor material can be adjacent to the first semiconductor material, such that a junction is formed. The junction can be abrupt or graded. In a graded junction, the first material blends with the second material in the junction, providing a graded change in material. In contrast, in an abrupt junction there is little or substantially no blending of the materials.

The second semiconductor material of the nanocrystal can include a Group II-VI compound, a Group II-V compound, a Group III-VI compound, a Group III-V compound, a Group IV-VI compound, a Group I-III-VI compound, a Group II-IV-VI compound, a Group II-IV-V compound, or mixtures thereof. For example, the second semiconductor material can include ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof. For example, ZnS, ZnSe or CdS overcoatings can be grown on CdSe or CdTe nanocrystals.

An alloy can have the formula $M^1_i M^2_j M^3_k E^1_x E^2_y E^3_z$. $M^1$, $M^2$ and $M^3$ can each independently be a group I, group II, group III, or group IV element. $E^1$, $E^2$ and $E^3$ each independently can be a group IV, group V, or group VI element. For example, $M^1$, $M^2$ and $M^3$ can each independently be magnesium, zinc, copper, cadmium, mercury, aluminum, gallium, indium, thallium, silicon, germanium, tin, or lead; and $E^1$, $E^2$ and $E^3$ each independently can be silicon, germanium, tin, lead, nitrogen, phosphorus, arsenic, antimony, oxygen, sulfur, selenium, or tellurium.

The values of i, j, k, x, y, and z are positive or zero. In some instances, the value of i, j, k, x, y, or z can be an integer. For example, an alloy can have the formula $M^1 E^1_x E^2_y$. In this formula, the value of i is 1 and the values of j and k are zero (alternatively, $M^1$, $M^2$ and $M^3$ are identical), and the value of z is zero (alternatively, $E^2$ and $E^3$ are identical). The sum of i, j and k can be an integer, and the sum of x, y and z can be an integer. For example, if the sum of x and y is 1, the preceding formula can be expressed as $M^1 E^1_x E^2_{1-x}$. In another example, an alloy can have the formula $M^1_i M^2_{1-i} E^1$. An alloy can have the formula $M^1_i M^2_j M^3_k E^1_x$ or $M^1_i M^2_j M^3_k E^1_x E^2_y$.

A nanocrystal having a central region and a distal region (or regions) can be described by a radius ratio. The radius ratio can be defined as the ratio of the radius of the distal region to the radius of the central region. The central region can have a radius in the range of 1 nm to 7 nm (such as between 1.5 nm and 5 nm), and the distal regions can have a radius in the range of 1 nm to 10 nm (such as between 1.5 nm and 5 nm). Accordingly, a barbell-shaped nanocrystal can have a radius ratio in the range of 0.1 to 10 (such as between 0.3 and 3.5). In some embodiments the radius ratio can be about 1. In other embodiments it can be substantially different than about 1, such as, for example, between 0.1 and 0.95 or between 1.05 and 10.

The junction between two semiconductor materials can have different configurations depending on the shape of the nanocrystal. For example, a spherical nanocrystal can have a spherical core of a first semiconductor material coated with a shell of a second semiconductor material. A rod shaped nanocrystal can have a rod of a first semiconductor material and a second semiconductor material. The second semiconductor material can coat the length and ends of the rods substantially evenly. Alternatively, the length and ends of the rod can be coated to different degrees. In particular, the ends of the rod can coated to a greater degree than the length of the rod. The ends of the rod each can be coated by an approximately spherical region of a second semiconductor material. In this case, the nanocrystal can have a barbell shape.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, CdSe can be tuned in the visible region and InAs can be tuned in the infrared region.

The population of nanocrystals can have a narrow size distribution. The population can be monodisperse and can exhibit less than a 15% rms deviation in size of the nanocrystals, preferably less than 10%, more preferably less than 5%. Spectral emissions in a narrow range of between 10 and 150 nm full width at half max (FWHM) can be observed (in other words, FWHM of less than 0.05 eV, or of less than 0.03 eV). Semiconductor nanocrystalscan have emission quantum efficiencies of greater than 2%, 5%, 10%, 20%, 40%, 60%, 70%, or 80%.

The method of manufacturing a nanocrystal can be a colloidal growth process and can produce a monodisperse particle population. Colloidal growth occurs by rapidly injecting an M donor(s) and an E donor(s) into a hot coordinating agent. In another variation, the M donor or M donors are dissolved in a hot coordinating agent, and an E donor or E donors are rapidly injected. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. Preparation and manipulation of nanocrystals are described, for example, in U.S. Pat. No. 6,322,901, which is incorporated by reference in its entirety.

The nanocrystal is a member of a population of nanocrystals. As a result of the discrete nucleation and controlled growth, the population of nanocrystals obtained can have a narrow, monodisperse distribution of sizes. The process of controlled growth and annealing of the nanocrystals in the coordinating agent that follows nucleation can also result in uniform surface derivatization and regular core structures. As the size distribution sharpens, the temperature can be raised to maintain steady growth. By adding more M donor or E donor, the growth period can be shortened.

The M donor(s) can be an inorganic compound, an organometallic compound (e.g., an alkyl metal compound such as triethyl gallium or trimethyl indium), or elemental metal. The inorganic compound can be a salt (e.g., a carboxylate salt, an acetylacetonate salt, a metal halide, a metal oxide, a metal alkoxide, and the like). The salt can be combined with a coordinating agent, such as an amine. See, for example, U.S. Pat. No. 6,576,291, which is incorporated by reference in its entirety. M can be cadmium, zinc, copper, magnesium, mercury, aluminum, gallium, indium or thallium. The E donor(s) can be a compound capable of reacting with the M donor to form a material with the general formula $M^1_i M^2_j M^3_k E^1_x E^2_y E^3_z$. Typically, the E donor is a chalcogenide donor or a pnictide donor, such as a phosphine chalcogenide, a bis(silyl) chalcogenide, dioxygen, an ammonium salt, or a tris(silyl) pnictide. Suitable E donors include dioxygen, bis(trimethylsilyl) selenide ($(TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl)telluride ($(TMS)_2Te$), bis(trimethylsilyl)sulfide ($(TMS)_2S$), a trialkyl phosphine sulfide such as (tri-n-octylphosphine) sulfide (TOPS), an ammonium salt such as an ammonium halide (e.g., $NH_4Cl$), tris(trimethylsilyl) phosphide ($(TMS)_3P$), tris(trimethylsilyl) arsenide ($(TMS)_3As$), or tris(trimethylsilyl) antimonide ($(TMS)_3Sb$). In certain embodiments, the M donor and the E donor can be moieties within the same molecule.

A coordinating agent can help control the growth of the nanocrystal. The coordinating agent is a compound having a donor lone pair that, for example, has a lone electron pair available to coordinate to a surface of the growing nanocrystal. The coordinating agent can be a solvent. Solvent coordination can stabilize the growing nanocrystal. Typical coordinating agents include alkyl phosphines, alkyl phosphine oxides, alkyl phosphonic acids, or alkyl phosphinic acids, however, other coordinating agents, such as pyridines, furans, and amines may also be suitable for the nanocrystal production. Examples of suitable coordinating agents include pyridine, tri-n-octyl phosphine (TOP) and tri-n-octyl phosphine oxide (TOPO). Technical grade TOPO can be used.

Nanocrystal shape can be determined by synthesis conditions, notably by the coordinating solvent(s) present during nanocrystal synthesis. The nanocrystal can be a sphere, rod, disk, or other shape. See, e.g., U.S. Pat. Nos. 6,225,198; 6,306,736; and 6,855,202, each of which is incorporated by reference in its entirety. Nanocrystal shape can be further controlled by the conditions under which a second semiconductor material is added to the nanocrystal.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average size, a population having a desired average nanocrystal size can be obtained.

The particle size distribution can be further refined by size selective precipitation with a poor solvent for the nanocrystals, such as methanol/butanol as described in U.S. Pat. No. 6,322,901, incorporated herein by reference in its entirety. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean size, preferably 10% rms deviation or less, and more preferably 5% rms deviation or less.

A cap including a second semiconductor material can be added to the nanocrystal. A capping process is described, for example, in U.S. Pat. No. 6,322,901, which is incorporated by reference in its entirety. By adjusting the temperature of the reaction mixture during capping and monitoring the absorption spectrum of the core, capped materials having high emission quantum efficiencies and narrow size distributions can be obtained. The shape of the cap can depend on the shape of the initial nanocrystal and the capping conditions used. For example, a cap grown on an approximately spherical nanocrystal can also be approximately spherical. In this case, the cap can substantially coat the spherical nanocrystal. If the initial nanocrystal is rod-shaped, the cap can be grown primarily on the ends of the rod and very little of the second semiconductor material added along the axis of the rod. A rod-shaped nanocrystal can be capped with a rod-shaped cap, or with an approximately spherical cap. Capping conditions, such as solvent composition and temperature, can determine the shape of the cap. For example, when caps are added under conditions that favor rod-shaped growth, rod-shaped caps can be formed; in contrast, approximately spherical caps are formed when the capping conditions favor approximately spherical growth.

It can be advantageous to purify nanocrystals before a second material is added to the nanocrystal. As discussed above, the nanocrystals can be purified by size-selective precipitation. After purification the nanocrystals can be treated with an etching agent. The etching agent can reduce the number of defect sites on the nanocrystals. Defect sites can act as undesired nucleation sites during addition of a second material. In making barbell-shaped nanocrystals, nucleation is desired at the ends of rods, but defect sites can cause nucleation along the length of a rod. Because the etching agent reduces the number of defect sites, the resulting barbells will have fewer warts along the length of the rods than barbells prepared without a prior etching treatment. The etching agent can be an amine, such as a primary amine, e.g., octylamine. An etching agent can be included during addition of a second semiconductor material to a nanocrystal.

Two-pot synthesis of nanocrystals can improve (compared to one-pot synthesis) the quality of the heterojunction by minimizing contamination of the one material with the other material. Adding the nanocrystals at temperatures normally used for core growth (rather than nucleation) can reduce overcoating of a rod (e.g., along the length of the rod) by the second semiconductor material.

The outer surface of the nanocrystal can include a layer of compounds derived from the coordinating agent used during the growth process. The surface can be modified by repeated exposure to an excess of a competing coordinating group to form an overlayer. For example, a dispersion of the nanocrystal can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

In general, a ligand for a nanocrystal can include a first monomer unit including a first moiety having affinity for a surface of the nanocrystal, a second monomer unit including a second moiety having a high water solubility, and a third monomer unit including a third moiety having a selectively reactive functional group or a selectively binding functional group. In this context, a "monomer unit" is a portion of a polymer derived from a single molecule of a monomer. For example, a monomer unit of poly(ethylene) is —$CH_2CH_2$—, and a monomer unit of poly(propylene) is —$CH_2CH(CH_3)$—. A "monomer" refers to the compound itself, prior to polymerization, e.g., ethylene is a monomer of poly (ethylene) and propylene of poly(propylene).

A selectively reactive functional group is one that can form a covalent bond with a selected reagent under selected conditions. One example of a selectively reactive functional group is a primary amine, which can react with, for example, a succinimidyl ester in water to form an amide bond. A selectively binding functional group is a functional group that can form a noncovalent complex with a selective binding counterpart. Some well-known examples of selectively binding functional groups and their counterparts include biotin and streptavidin; a nucleic acid and a sequence-complementary nucleic acid; FK506 and FKBP; or an antibody and its corresponding antigen.

A moiety having high water solubility typically includes one or more ionized, ionizable, or hydrogen bonding groups, such as, for example, an amine, an alcohol, a carboxylic acid, an amide, an alkyl ether, a thiol, or other groups known in the art. Moieties that do not have high water solubility include, for example, hydrocarbyl groups such as alkyl groups or aryl groups, haloalkyl groups, and the like. High water solubility can be achieved by using multiple instances of a slightly soluble group: for example, diethyl ether is not highly water soluble, but a poly(ethylene glycol) having multiple instances of a —$CH_2$—O—$CH_2$— alkyl ether group can be highly water soluble.

For example, the ligand can include a polymer including a random copolymer. The random copolymer can be made using any method of polymerization, including cationic, anion, radical, metathesis or condensation polymerization, for example, living cationic polymerization, living anionic polymerization, ring opening metathesis polymerization, group transfer polymerization, free radical living polymerization, living Ziegler-Natta polymerization, or reversible addition fragmentation chain transfer (RAFT) polymerization. The random copolymer can include regions having each of the following formulae:

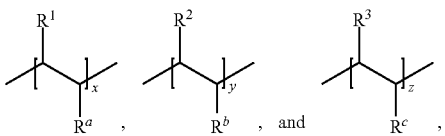

In these regions, $R^1$ is a first moiety having affinity for a surface of the nanocrystal, $R^2$ is a second moiety having a high water solubility, $R^3$ is a third moiety having a selectively reactive functional group or a selectively binding functional group, each of $R^a$, $R^b$, and $R^c$, independently, is substituted or unsubstituted alkyl, substituted or unsubstituted alkoxy, substituted or unsubstituted aryl, or substituted or unsubstituted aryloxy; and each of x, y, and z, independently, a positive integer.

Polyhistidine motifs can have high affinity a nanocrystal surface (e.g., when the surface includes Cd and/or Zn, or other Group II elements), and $His_6$-tags have been employed for facile and efficient derivatization of nanocrystals with peptides, dyes, and proteins. See Howarth, M.; Liu, W.; Puthenveetil, S.; Zheng, Y.; Marshall, L. F.; Schmidt, M. M.; Wittrup, K. D.; Bawendi, M. G.; Ting, A. Y., Monovalent, reduced-size quantum dots for imaging receptors on living cells. *Nat Meth* 2008, 5, (5), 397-399, Sapsford, K. E.; Pons, T.; Medintz, I. L.; Higashiya, S.; Brunel, F. M.; Dawson, P. E.; Mattoussi, H., Kinetics of Metal-Affinity Driven Self-Assembly between Proteins or Peptides and CdSe—ZnS Quantum Dots. *J. Phys. Chem. C.* 2007, 111, (11528-11538), Medintz, I. L.; Pons, T.; Delehanty, J. B.; Susumu, K.; Brunel, F. M.; Dawson, P. E.; Mattoussi, H., Intracellular delivery of quantum dot-protein cargos mediated by cell penetrating peptides. *Bioconjugate Chemistry* 2008, 19, (9), 1785-1795, and Aaron R. Clapp, I. L. M., Hedi Mattoussi, Förster Resonance Energy Transfer Investigations Using Quantum-Dot Fluorophores. *ChemPhysChem* 2006, 7, (1), 47-57, each of which is incorporated by reference in its entirety. A polymer rich with imidazole groups can achieve efficient and multi-dentate binding to a nanocrystal surface. The polyimidazole motif can be advantageous because it is not susceptible to the issues plaguing thiol-based chemistry, such as degradation by oxidation. Furthermore, multidentate binding by a polyhistidine can greatly enhance stability. See Yildiz, I.; McCaughan, B.; Cruickshank, S. F.; Callan, J. F.; Raymo, F. i. M., Biocompatible CdSe—ZnS Core-Shell Quantum Dots Coated with Hydrophilic Polythiols. *Langmuir* 2009, 25, (12), 7090-7096, which is incorporated by reference in its entirety. To promote water solubility and reduce non-specific binding (see Bentzen, E. L.; Tomlinson, I. D.; Mason, J.; Gresch, P.; Warnement, M. R.; Wright, D.; Sanders-Bush, E.; Blakely, R.; Rosenthal, S. J., Surface modification to reduce nonspecific binding of quantum dots in live cell assays. *Bioconjugate Chemistry* 2005, 16, (6), 1488-1494, which is incorporated by reference in its entirety.), a PEG derived monomer can be co-polymerized along with an imidazole-based monomer to form a co-polymer displaying both PEG and imidazole groups along the backbone. Using an additional monomer featuring an amine or a biotin functional group, a 3-component multifunctional co-polymer can be synthesized for nanocrystal water solubilization and derivatization.

Radical addition fragmentation chain transfer (RAFT) polymerization chemistry can provide molecular weight control and narrow polydispersity of the co-polymer. The RAFT agent can also mediate polymerization of a wide diversity of monomers for controlled co-polymerization. See Chiefari, J.; Chong, Y. K.; Ercole, F.; Krstina, J.; Jeffery, J.; Le, T. P. T.; Mayadunne, R. T. A.; Meijs, G. F.; Moad, C. L.; Moad, G.; Rizzardo, E.; Thang, S. H., Living free-radical polymerization by reversible addition-fragmentation chain transfer: The RAFT process. *Macromolecules* 1998, 31, (16), 5559-5562, which is incorporated by reference in its entirety. By tuning the ratio and composition of monomers, complex copolymers can be assembled with the desired properties for nanocrystal water solubilization and derivatization, form compact nanocrystals suitable for live cell and in-vivo imaging with extremely low non-specific binding and greatly enhanced stability and long-term shelf-life. By using a catechol group instead of imidazole for binding, iron oxide nanocrystals can also be solublized. The length of PEG chain can be chosen in part based on the size of the nanocrystal involved—larger nanocrystals can require longer PEG chains for solubility.

The method of imaging includes introducing a composition including a particle containing a semiconductor nanocrystal into a subject, exciting the particle with an excitation light source, detecting emission from the particle in short wavelength infrared (SWIR) spectrum at an imaging frequency of at least 6 fps, at least 20 fps, at least 30 fps, at least 40 fps, or at least 48 fps and generating a real-time image of an area surrounding of the subject from the detected SWIR emission, where the excitation spectrum is tunable. The semiconductor nanocrystal includes a InAs based core-shell particles where a core of a first semiconductor material and an overcoating of a second semiconductor material on the core wherein the first semiconductor material and the second semiconductor material are selected so that, upon excitation, one carrier is substantially confined to the core and the other carrier is substantially confined to the overcoating.

The disclosed imaging apparatus includes a semiconductor nanocrystal, wherein the nanomaterial comprising a nanocrystal, and an outer layer including a ligand, the ligand including a first monomer unit including a first moiety having affinity for a surface of the nanocrystal, a second monomer unit including a second moiety having a high water solubility; and a third monomer unit including a third moiety having a selectively reactive functional group or a selectively binding functional group, where the nanocrystal emits light in short wavelength infrared (SWIR) spectrum, and a real-time image of an area surrounding of the subject from the detected SWIR emission is generated.

An imaging composition can include the nanocrystal in a biocompatible carrier. For example, the biocompatible carrier can be saline or another biocompatible medium. The nanocrystal includes a ligand that stabilized the nanocrystal in the biocompatible carrier.

Method of Synthesis

Representative preparations for the synthesis of the InAs semiconductor nanocrystals used in the in-vivo imaging experiments are described.

Synthesis of InAs Cores:

InAs semiconductor nanocrystals cores were synthesized in a batch that provided material for several overcoating reactions to produce InAs(CdSe) or InAs(CdS) core shell semiconductor nanocrystals. The method of producing the InAs cores has not been reported in the literature. This method allows the synthesis of larger InAs cores than is otherwise possible using indium carboxylate precursors, and it gives excellent control over the final semiconductor nanocrystal size and size distribution by using continuous injection of arsenic precursors to grow the semiconductor nanocrystals larger while maintaining or improving Semiconductor nanocrystalsize distribution. The fact that control over semiconductor nanocrystal size is achieved by slow, continuous injection of arsenic precursors allows the precise and accurate production of semiconductor nanocrystals that emit at a specific wavelength.

In a typical procedure, 4 mmoles of Indium(III) acetate, 14 mmoles of myristic acid, and 20 mL of 1-octadecene were added to a 50 mL 4 neck round bottom flask. The flask was heated to 110° C. under vacuum (10 mtorr) for two hours to remove acetic acid and form a solution of indium (III) myristate. The indium myristate solution was heated under argon to 295° C.

An injection syringe containing 0.22 mmoles of tris (trimethylgermyl)arsine dissolved in 4 mL of tri-n-octylphosphine was prepared in a nitrogen glovebox and rapidly injected into the indium myristate solution at 295° C.

After 10 minutes, a syringe containing 0.72 mmoles of tris(trimethylgermyl)arsine dissolved in 1 mL of tri-n-octylphosphine and 4 mL of 1-octadecene was loaded into a syringe pump and the arsenic precursor solution was injected at 4 mL/hour at a temperature of 295° C. Substitution of the more commonly used tris(trimethylsilyl)arsine precursor in this step resulted in the formation of dark insoluble solids in the reaction solution. The semiconductor nanocrystal size was monitored during this step by removing aliquots from the solution. When the semiconductor nanocrystals reached the desired size, the precursor injection was stopped and the reaction was removed from heat.

The semiconductor nanocrystals were isolated by filtering the growth solution diluted in toluene through a 200 nm PTFE filter, then adding acetone to cause the semiconductor nanocrystals to precipitate out of solution and centrifuging. The semiconductor nanocrystals were dissolved in 20 mL hexane and stored for overcoating.

The InAsCdSeZnSe overcoating procedure is adapted from a published method. See Aharoni, A.; Mokari, T.; Popov, I.; Banin, U. "Synthesis of InAs/CdSe/ZnSe core/shell1/shell2 structures with bright and stable near-infrared fluorescence." *Journal of the American Chemical Society* 2006, 128, 257-64, which is incorporated by reference in its entirety. The InAs/CdS procedure is adapted from conditions described for making CdSe/CdS core shell semiconductor nanocrystals. See, Li, J. J.; Wang, Y. A.; Guo, W.; Keay, J. C.; Mishima, T. D.; Johnson, M. B.; Peng, X. "Large-Scale Synthesis of Nearly Monodisperse CdSe/CdS Core/Shell Nanocrystals Using Air-Stable Reagents via Successive Ion Layer Adsorption and Reaction" *Journal of the American Chemical Society* 2003, 125, 12567-12575, which is incorporated by reference in its entirety.

Overcoating InAs Semiconductor Nanocrystals:

The InAs semiconductor nanocrystals were overcoated as follows:

InAs(CdSeZnSe) (adopted from Aharoni et al., JACS, 2006)

44 nmoles of InAs cores in hexane (prepared as described above) were added to 4 mL of 1-octadecene, 3 mL of oleylamine, and 0.5 mL of 0.05M trioctylphosphine selenide in TOP (TOPSe). The solution was degassed at 100° C. under vacuum for 40 minutes, 15 mtorr, to remove the hexane, then heated to 230° C. under argon. 0.47 mL of solutions of 0.05M cadmium oleate and 0.05M TOPSe were injected side by side using a syringe pump at 1 mL/hr at 230 C. Then 0.6 mL of 0.05M diethylzinc was added and the temperature was raised to 250 C. After 15 minutes, 0.6 mL of 0.05M TOPSe was added. After 15 minutes, 0.75 mL of 0.05M diethylzinc was added. After 10 minutes, 0.95 mL of 0.04M Se dissolved in ODE was added. After 15 minutes, 1 mL of oleic acid was injected. After 13 minutes, 0.95 mL of diethylzinc was added. After another 13 minutes, 1.2 mL of 0.04M ODE-Se was added. The temperature was raised to 290 C for 25 minutes and then the reaction mixture was cooled. The quantum yield was found to be 30% using an integrating sphere. The PL peak was at ~1075 nm.

InAs(CdS):

The following procedure uses the precursors and temperatures described in Li(JACS, 2003), but doesn't use the "SILAR" technique, and I use it to overcoat InAs cores.b90 nmoles of InAs cores in hexane were added to 10 mL of ODE. The solution was degassed under vacuum at 100° C. to remove the hexane. 8.2 mL of 0.05M solutions of cadmium oleate and sulfur in octadecene were added side by side using a syringe pump at 5 mL/hr at a temperature of 230° C. The PL peak was found to be 1150 nm, with a quantum yield of 35% in chloroform.

Water Soluble SWIR Dots 1,2-dioleoyl-sn-glycero-3-phosphoethanolamine-N-[methoxy(polyethylene glycol)-2000] ammonium salt (PEG-lipid, MW: ~2800 g/mol) in chloroform solution was purchased from Avanti Polar Lipids. 1 mg of SWIR semiconductor nanocrystals (dry weight) was dissolved in 0.5 mL of chloroform and 400 μL of PEG-lipid in chloroform (25 mg/mL) were added (1:10 semiconductor nanocrystals to PEG-lipid). The mixture was vortexed at 2000 RPM for 1 min yielded a homogeneous solution, which was dried in vacuo. The pellet was then dispersed in 2 mL PBS 1× or isotonic saline solution and ultra-sonicated (Microson ultrasonic cell disruptor) for 5 min if needed. The solution was filtered through a 200 nm filter.

Setup

Video-rate imaging was performed using a homebuilt setup. FIG. 1 shows a schematic of the imaging apparatus. For reflection-mode imaging, an incandescent light bulb was used.

Fluorescence Imaging

For fluorescence imaging, an 808 nm 10 W laser (Opto Engine, MDL-F-808) was defocused with a f=75 mm planoconcave fused-silica lens (Thor Labs, LC1582-B) and ground-glass diffuser (Thor Labs), either 220 grit to achieve 20 mW/cm$^2$ or 1500 grit to achieve approximately 50 mW/cm$^2$ of flux over the sample area when run at full power. The light reflected or emitted by the sample under study was reflected off an aluminum-backed minor (McMaster-Carr) and imaged on an InGaAs focal plane (Princeton Instruments, NIRvana) using various C-mount objectives (Thor Labs) and different longpass filters (Thorlabs) to filter out the 808 nm excitation light. During experiments, individual frames were collected with integration times ranging from 5 ms-10 s.

For spectrally resolved imaging a liquid crystal tunable filter (LCTF) with a 20 nm bandwidth (VariSpec LNIR, Cambridge Research instruments/Perkin Elmer) was mounted in front of the objective. Alternatively a motorized filter wheel equipped either with band- or longpass filters (Thorlabs) was used instead of the LCTF.

Microscope Setup

Nikon Ti-E Inverted motorized Microscope equipped with a 850 nm LED with a condenser (Thorlabs) for excitation. Suitable dichroic and longpass filters (Thorlabs) for filtering out the excitation light. CFI Plan Apo Lambda 10× and CFI Apo 40× Objective WI NA 1.25 WD 0.18 objectives for imaging and MAC6000 motorized XY Stage. The InGaAs focal plane (Princeton Instruments, NIRvana) was mounted directly to the left side port.

Mouse Experiments

Mouse Handling and Injection

Male athymic nude mice were obtained from Charles River and The Jackson Laboratory. All mouse studies were approved by MITs Committee on Animal Care. For the injection of an SWIR semiconductor nanocrystal solution, a 30-gauge syringe needle connected to tubing was inserted into the lateral tail vein as catheter, allowing for bolus injection from outside the imaging setup. For anesthesia mice were injected intraperitoneally with Xylaxin and Ketamine (90-120 mg/kg Ketamine and 10 mg/kg Xylazine (Rompun).

For intraoperative imaging, the skin above the site of interest was removed to expose the operative field. For intravital microscopy, the organ of interest (liver, brown adipose tissue (BAT), spleen, kidney, lymph nodes, intestine, brain) was exposed by a small incision. The exposed organ was cover with a glass cover slip which was fixed with tissue adhesive. Animal was immobilized and was imaged with the customized microscopy techniques.

For imaging of awake mice the mice were injected with the SWIR semiconductor nanocrystals intravenously directly before imaging.

Imaging

Figure 2:
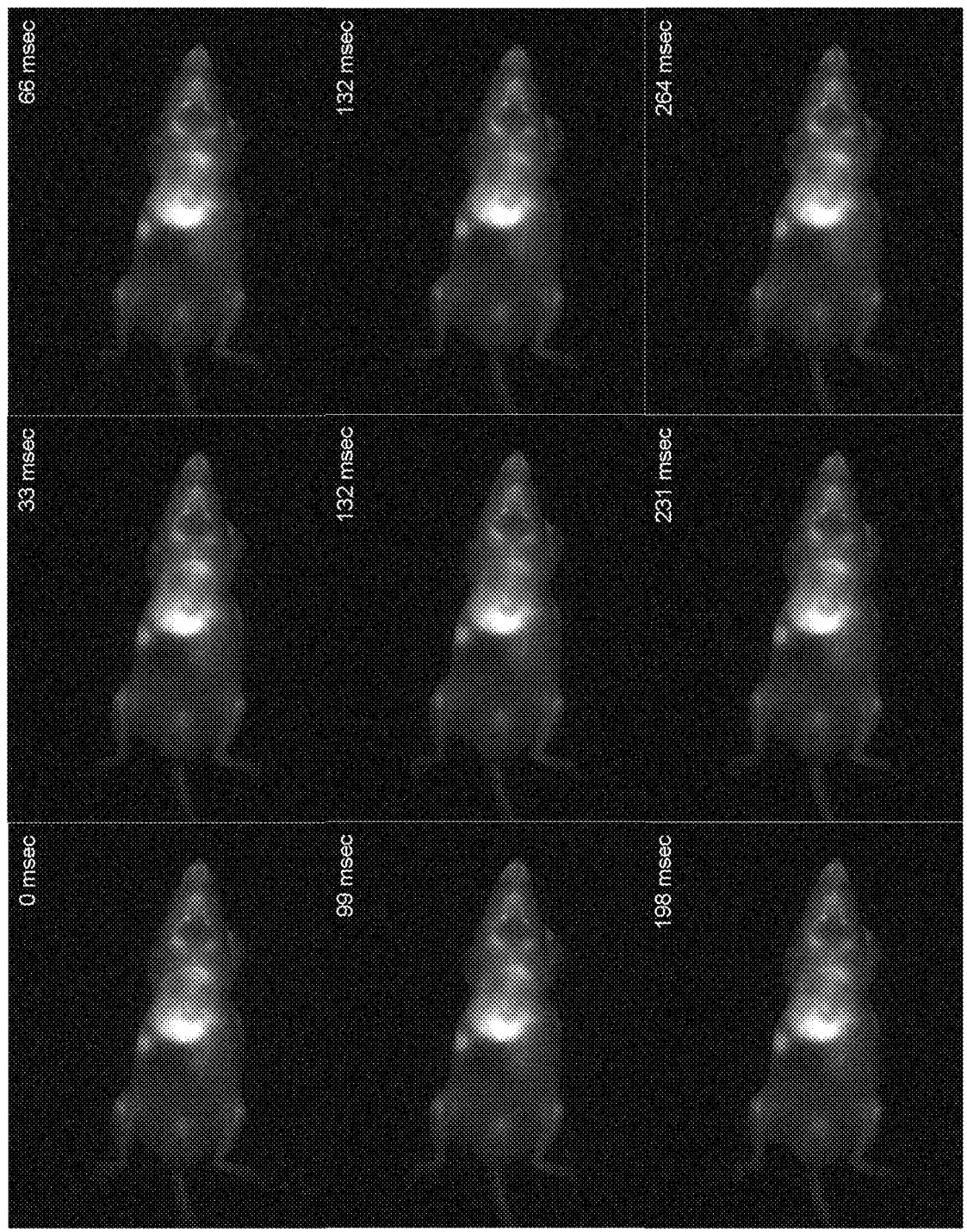
FIG. 2 depicts a non-invasive SWIR imaging.
Figure 2:
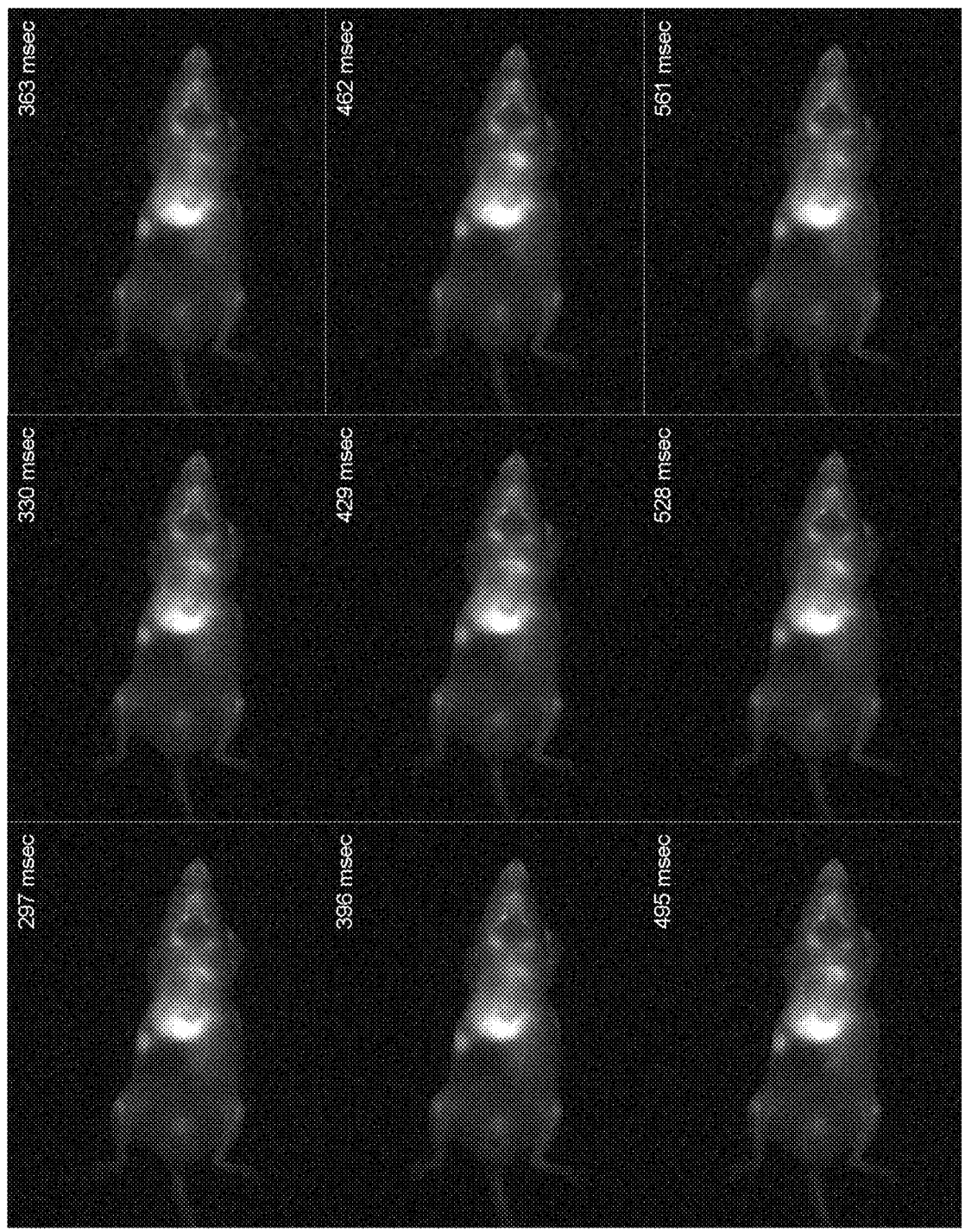
Figure 2:
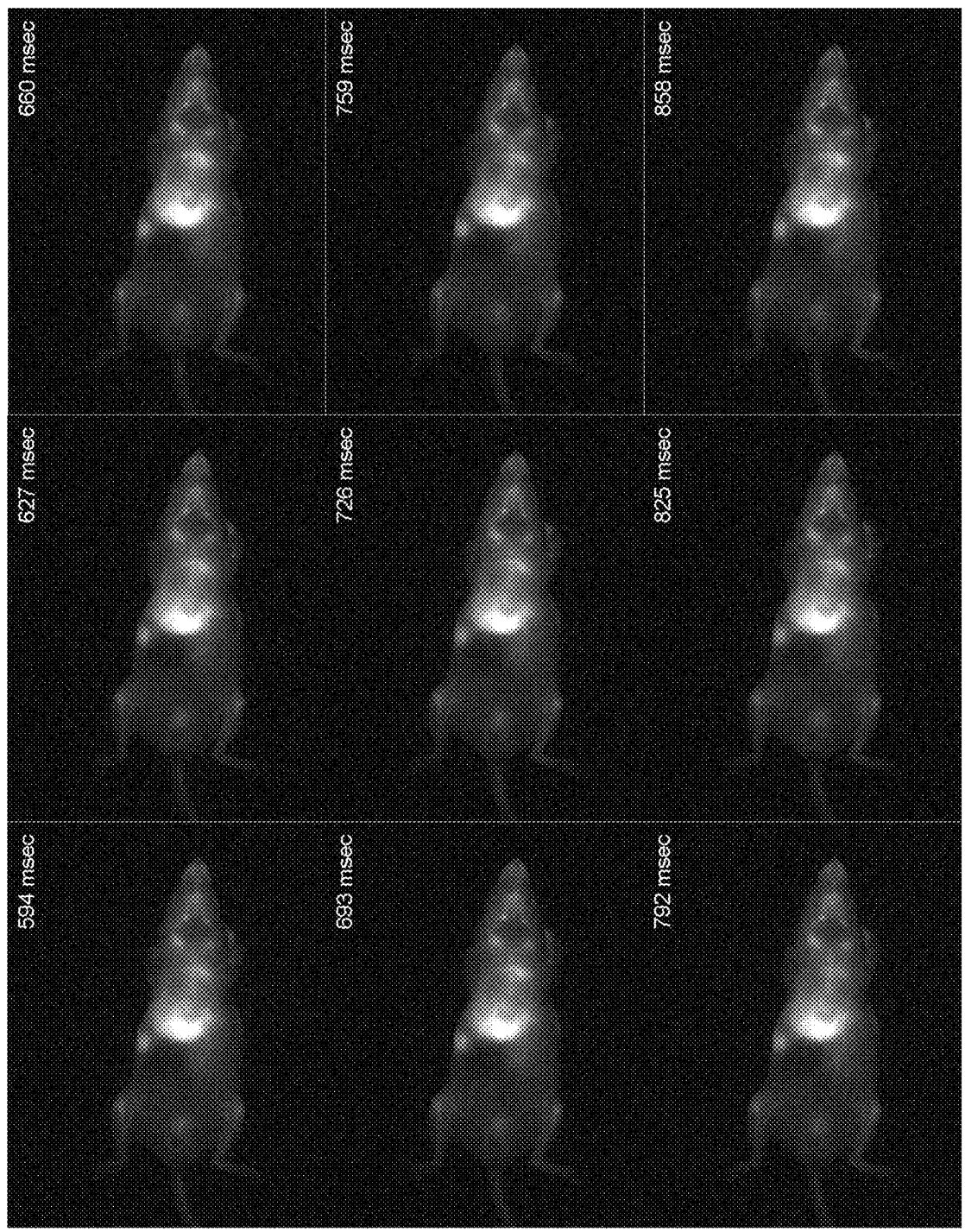
Figure 2:
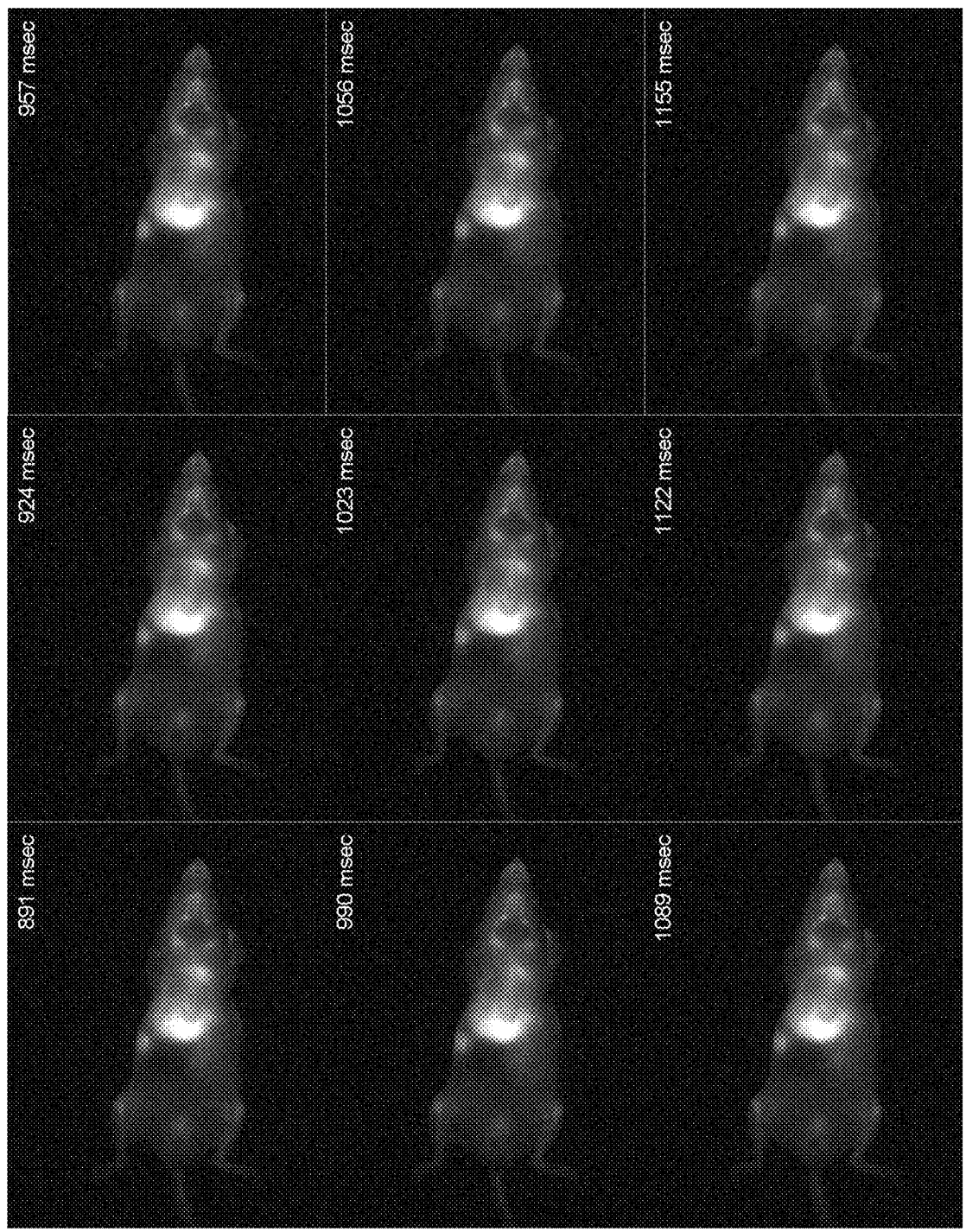
Figure 2:
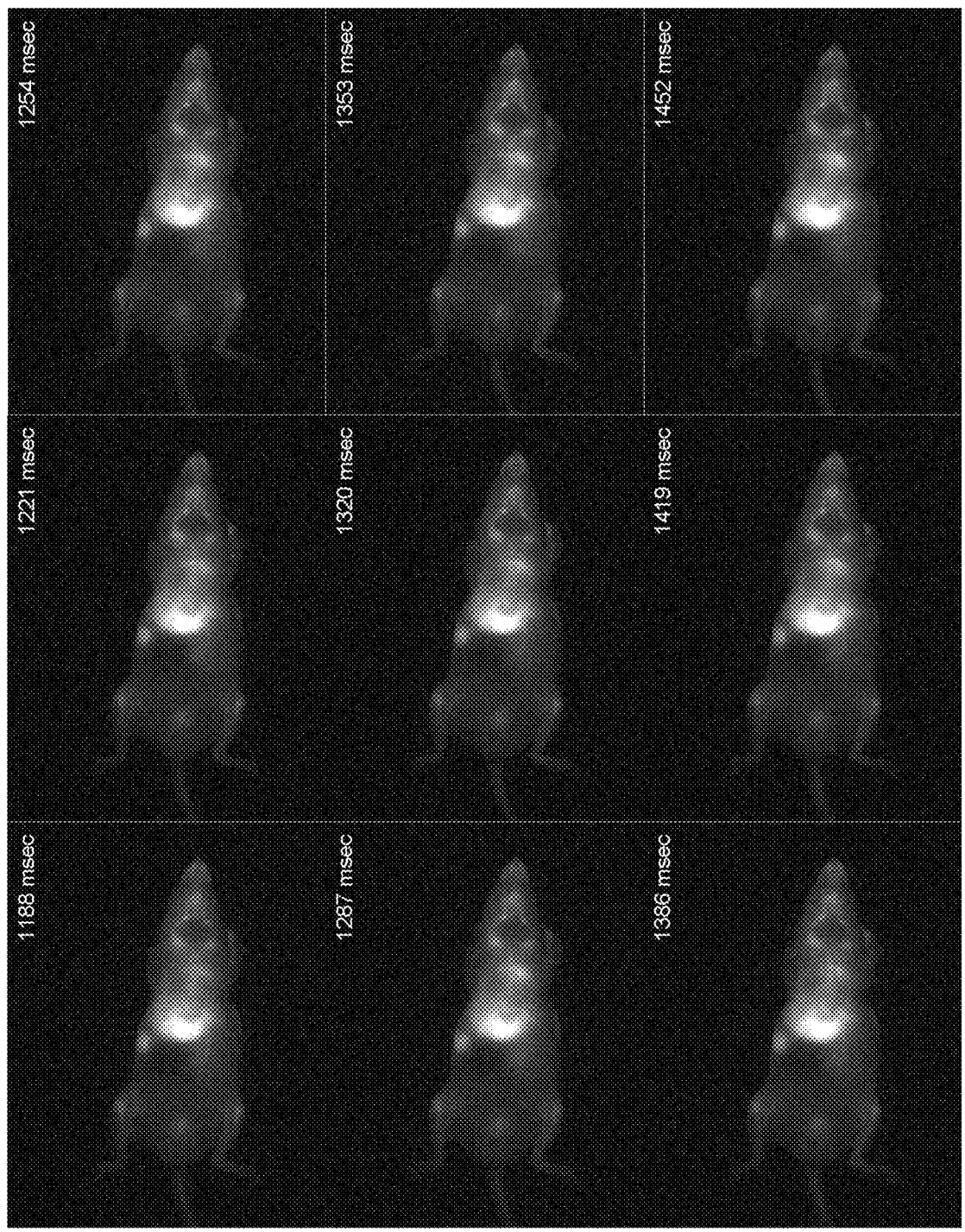
Figure 2:
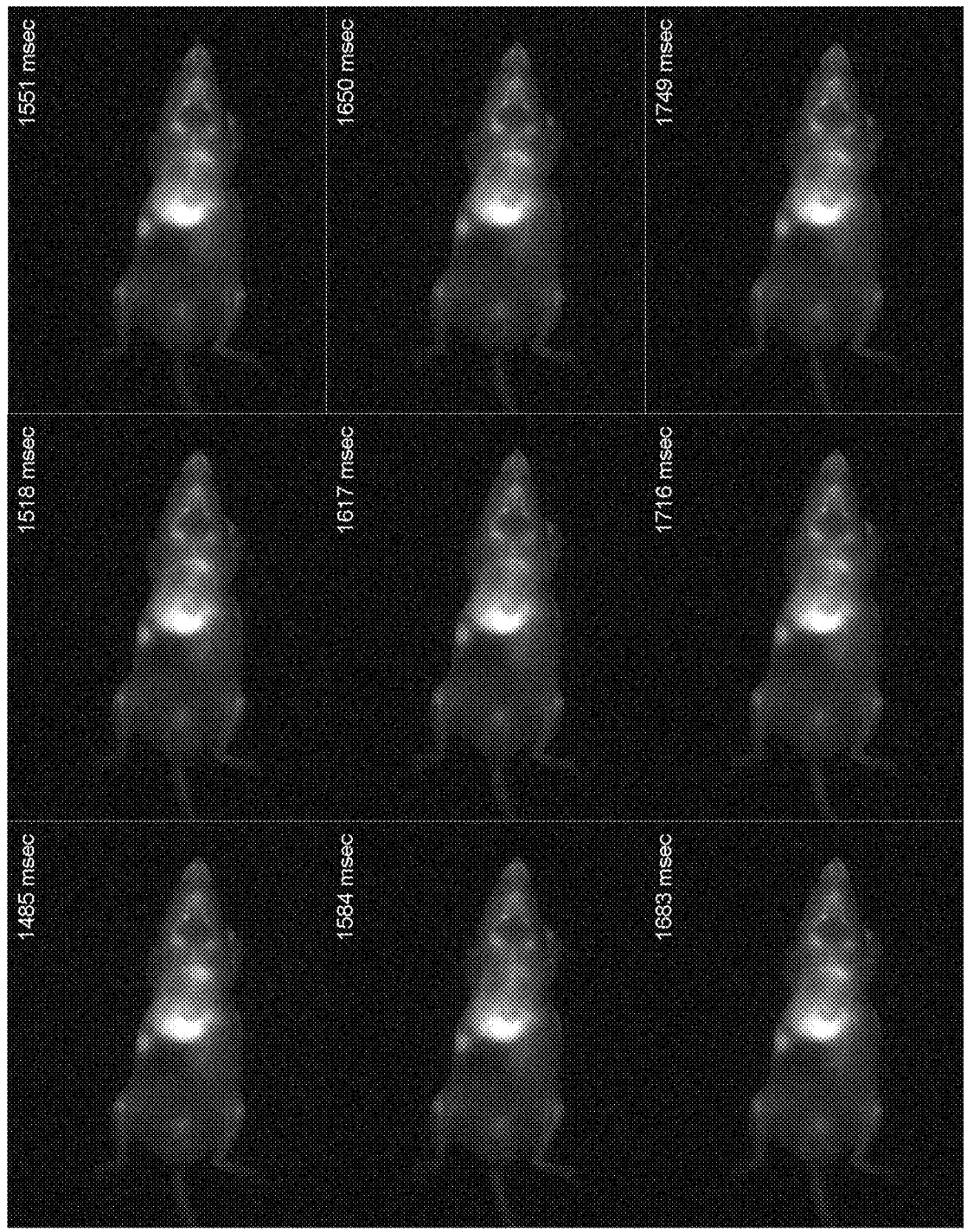
Figure 2:
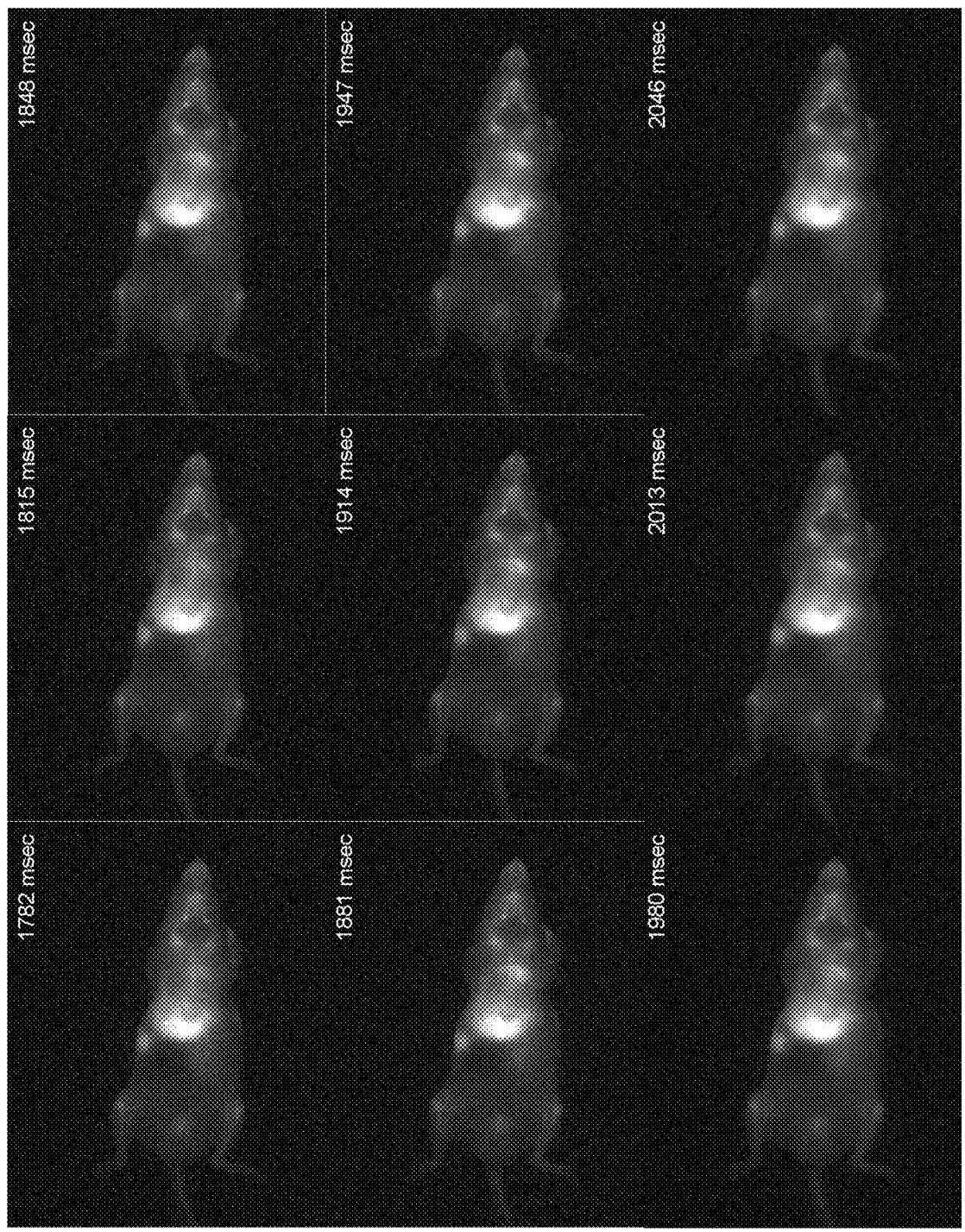
Figure 2:
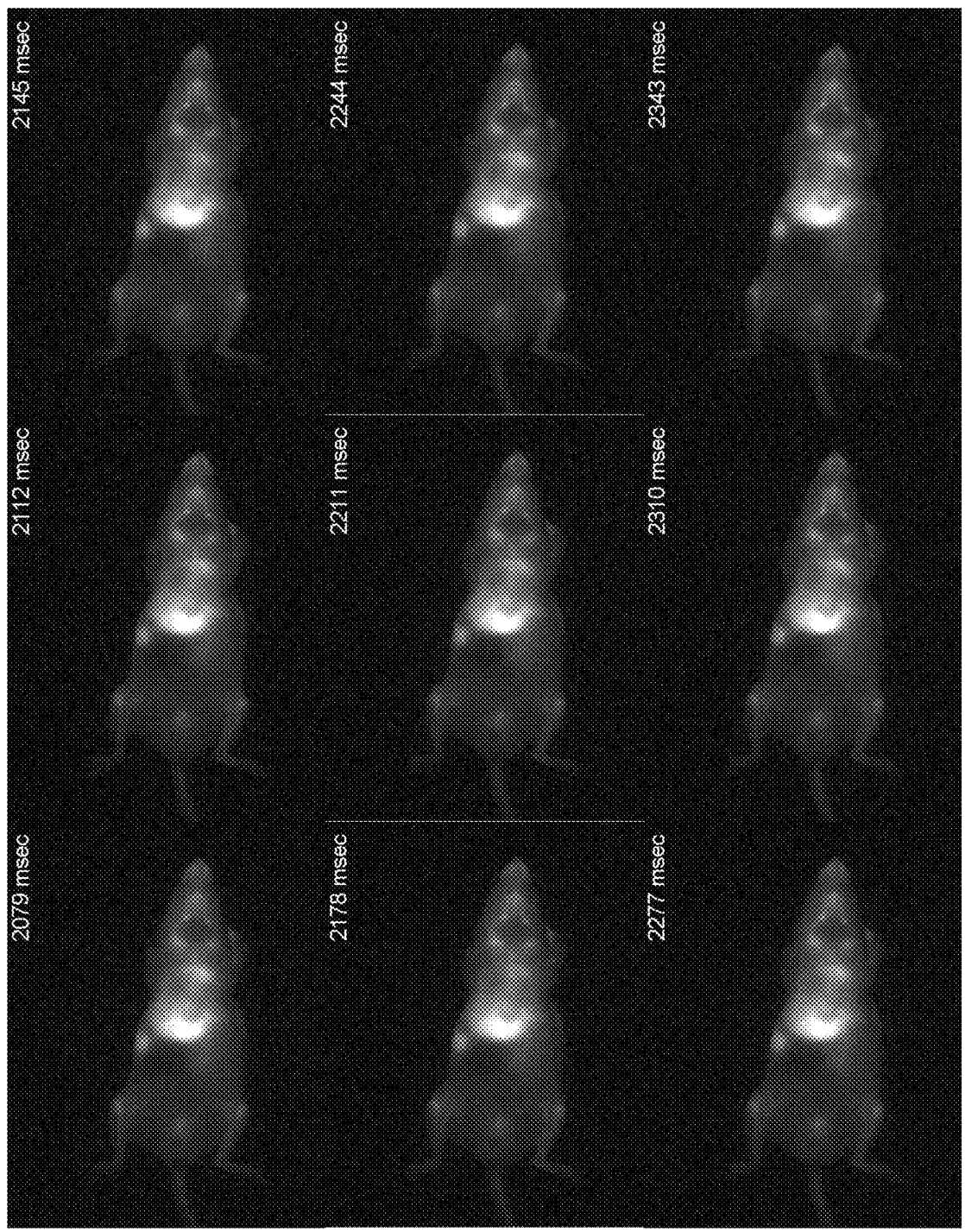
Figure 2:
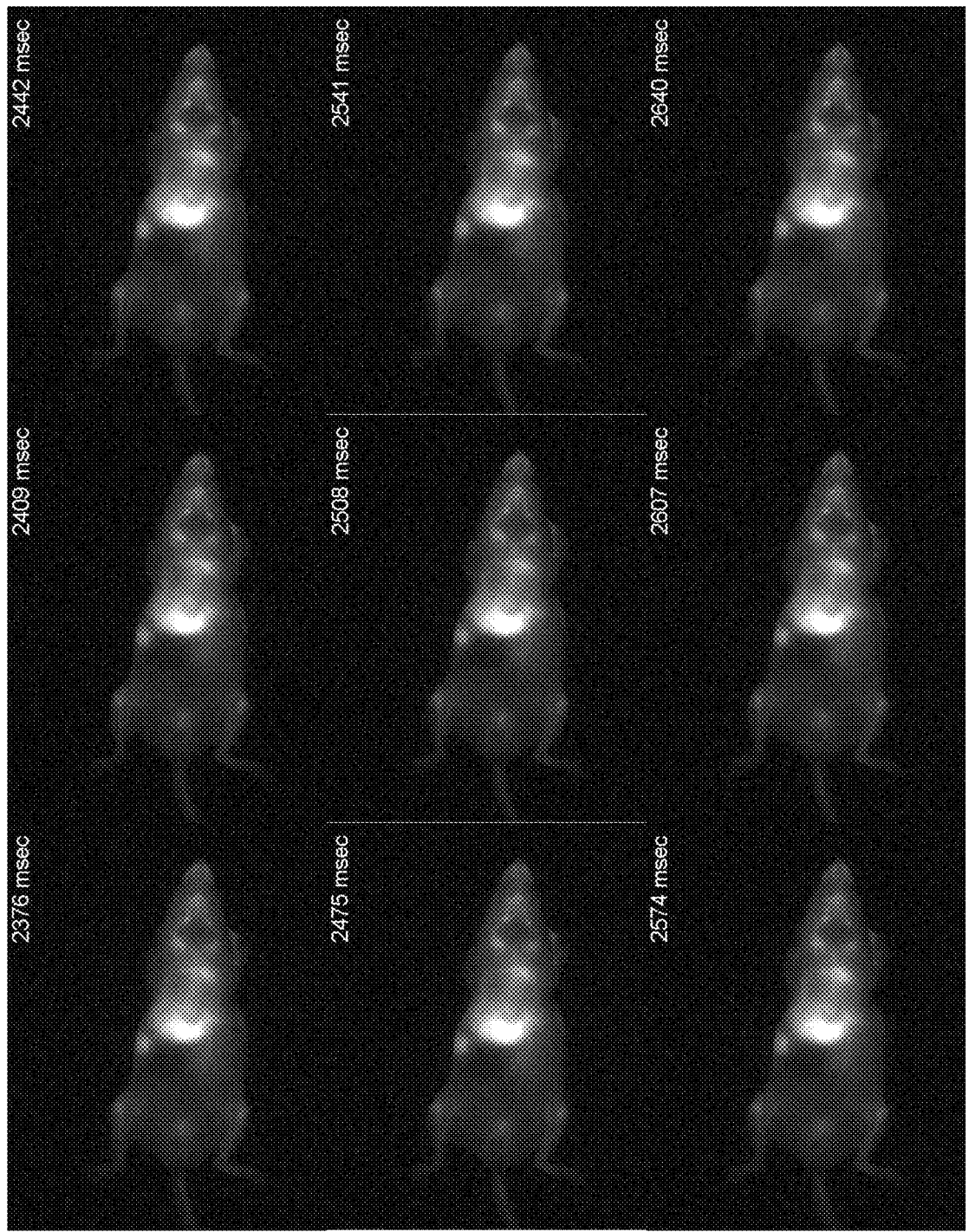
Figure 2:
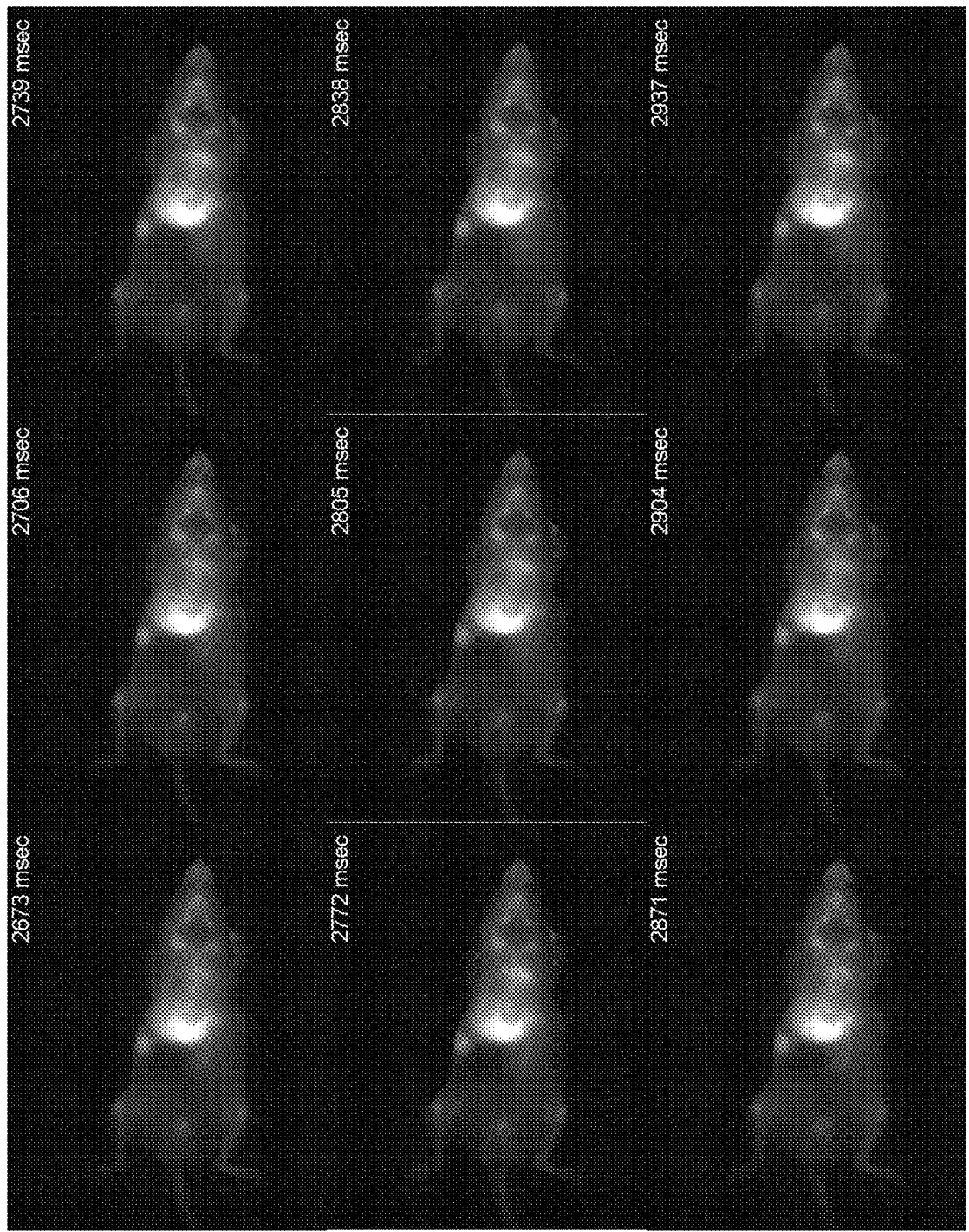
Figure 2:
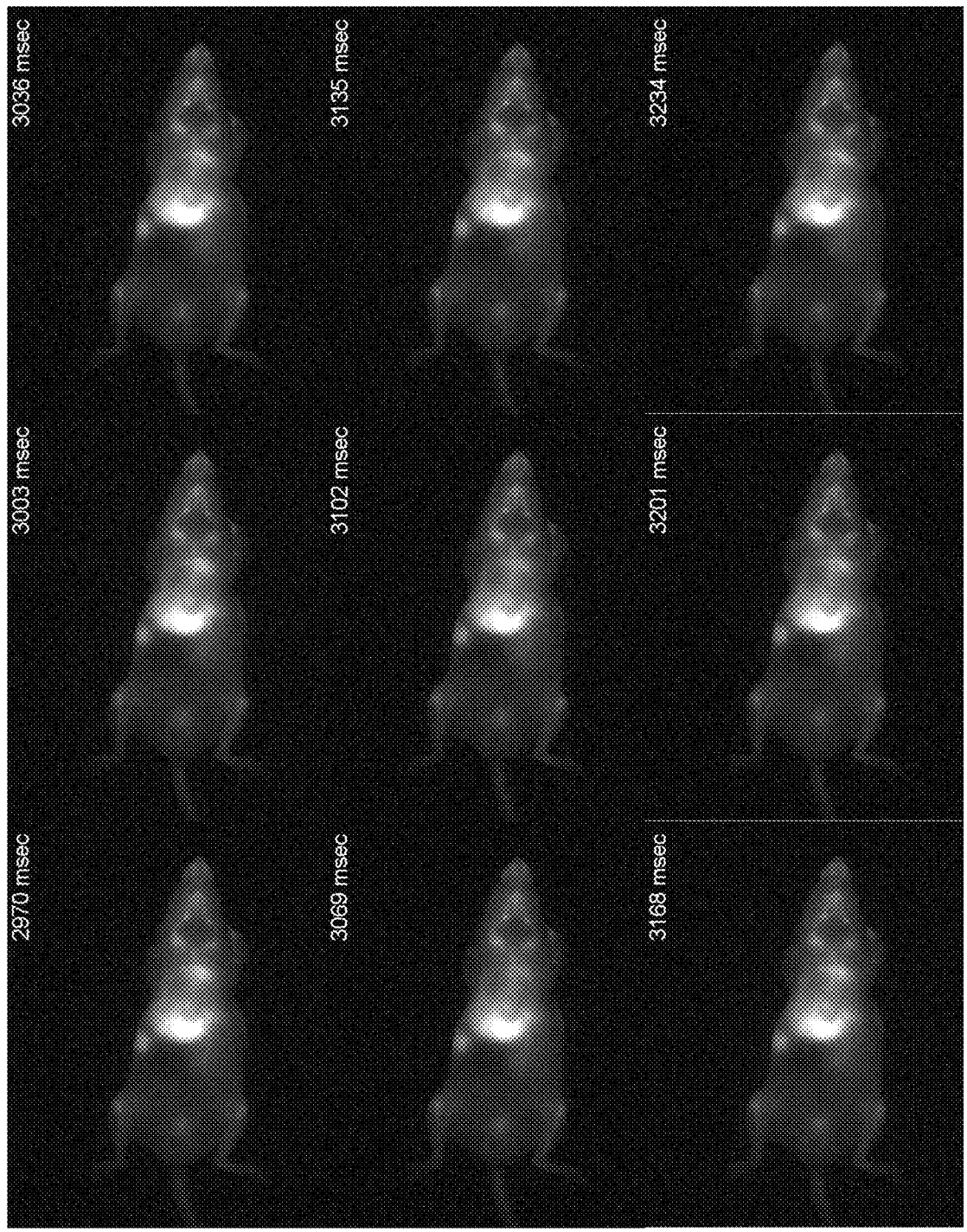
Figure 2:
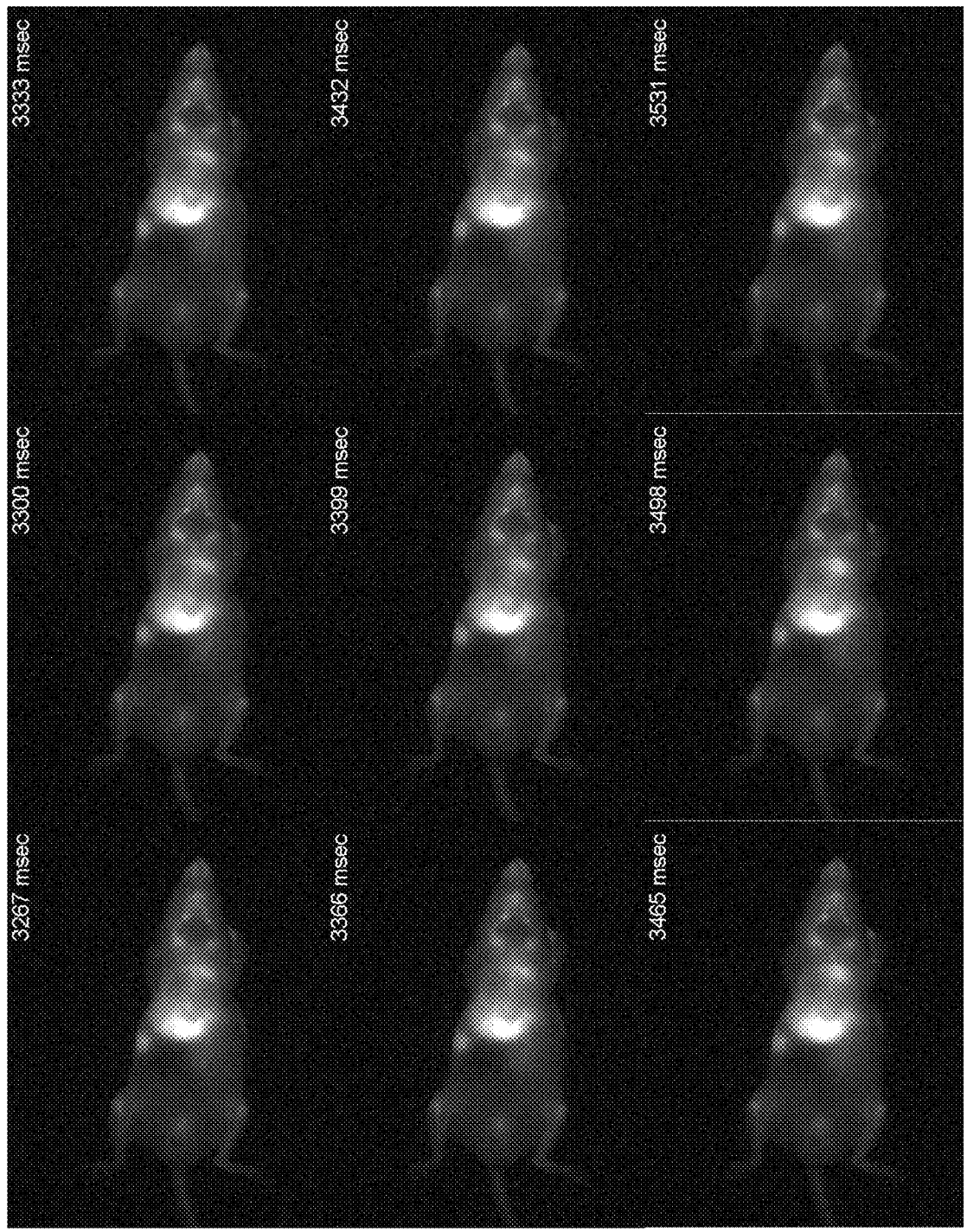
Figure 2:
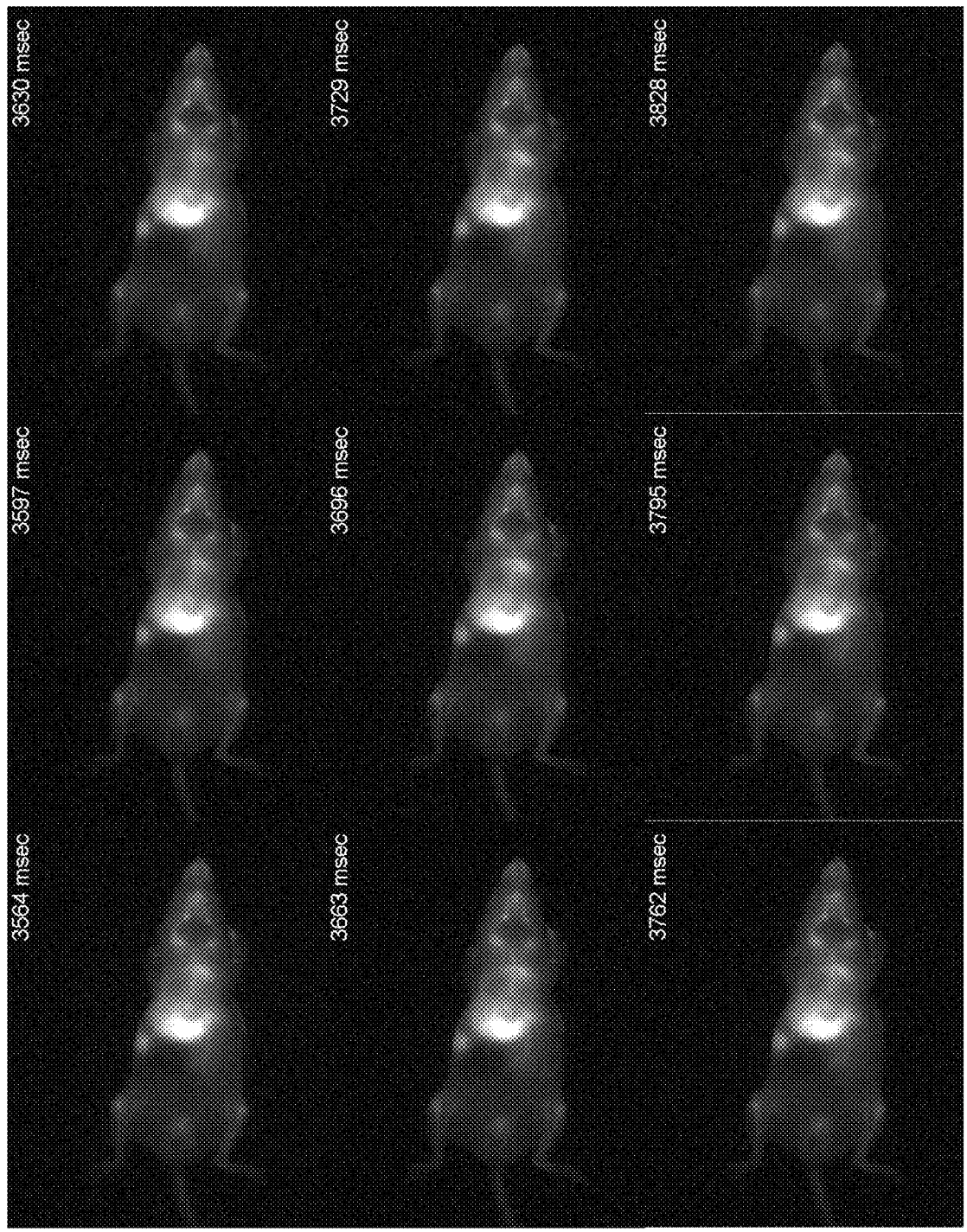
Figure 2:
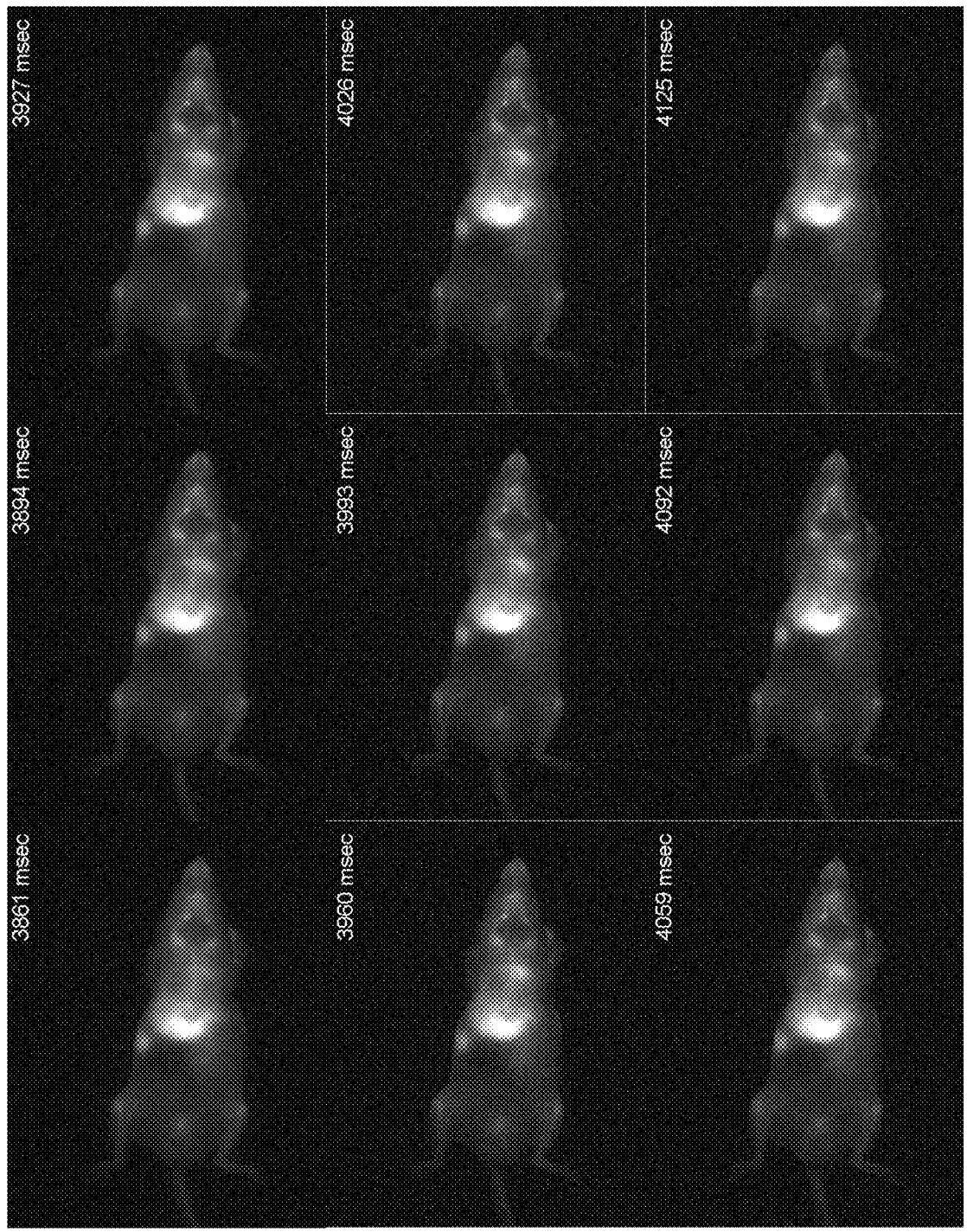
Figure 2:
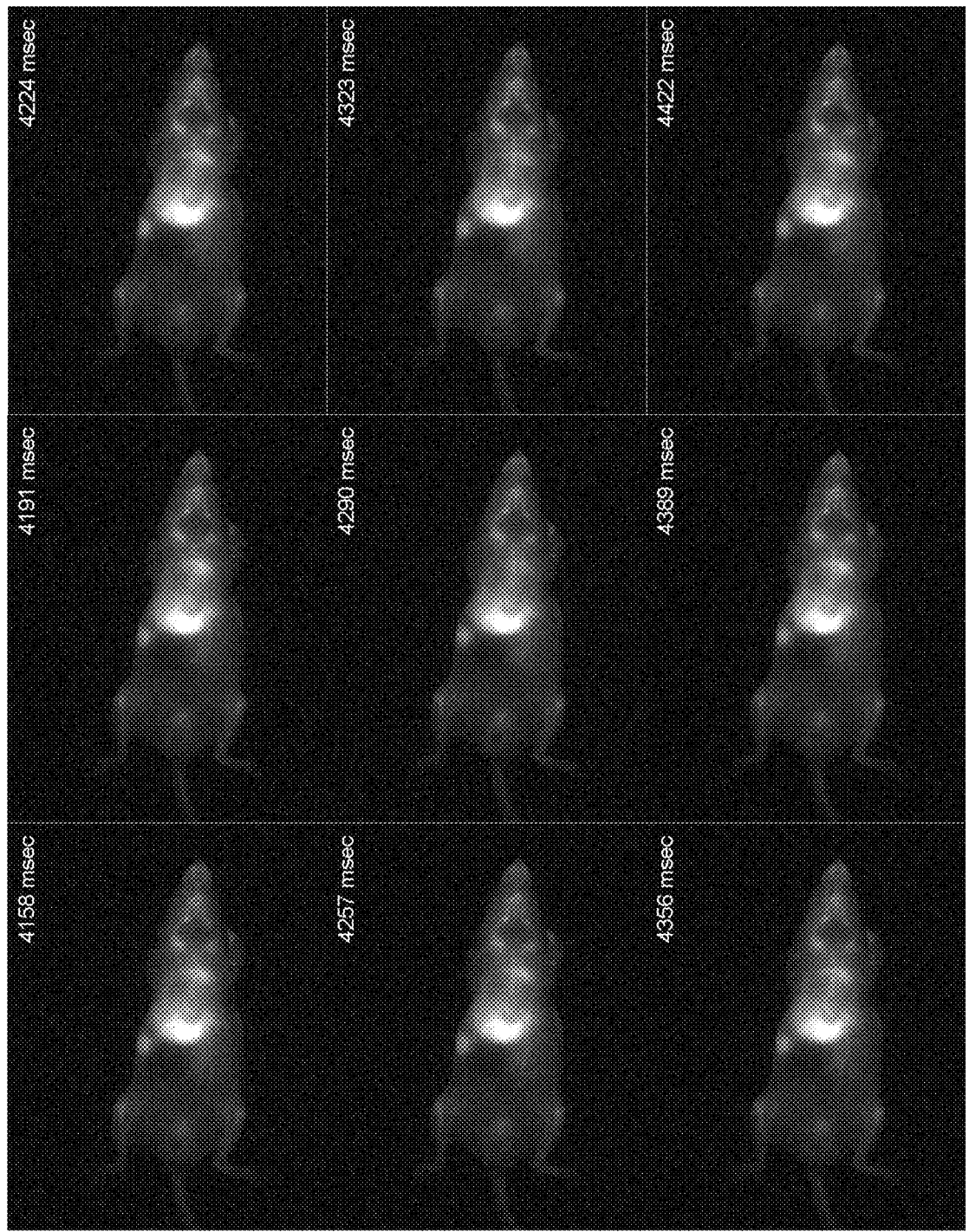
Figure 2:
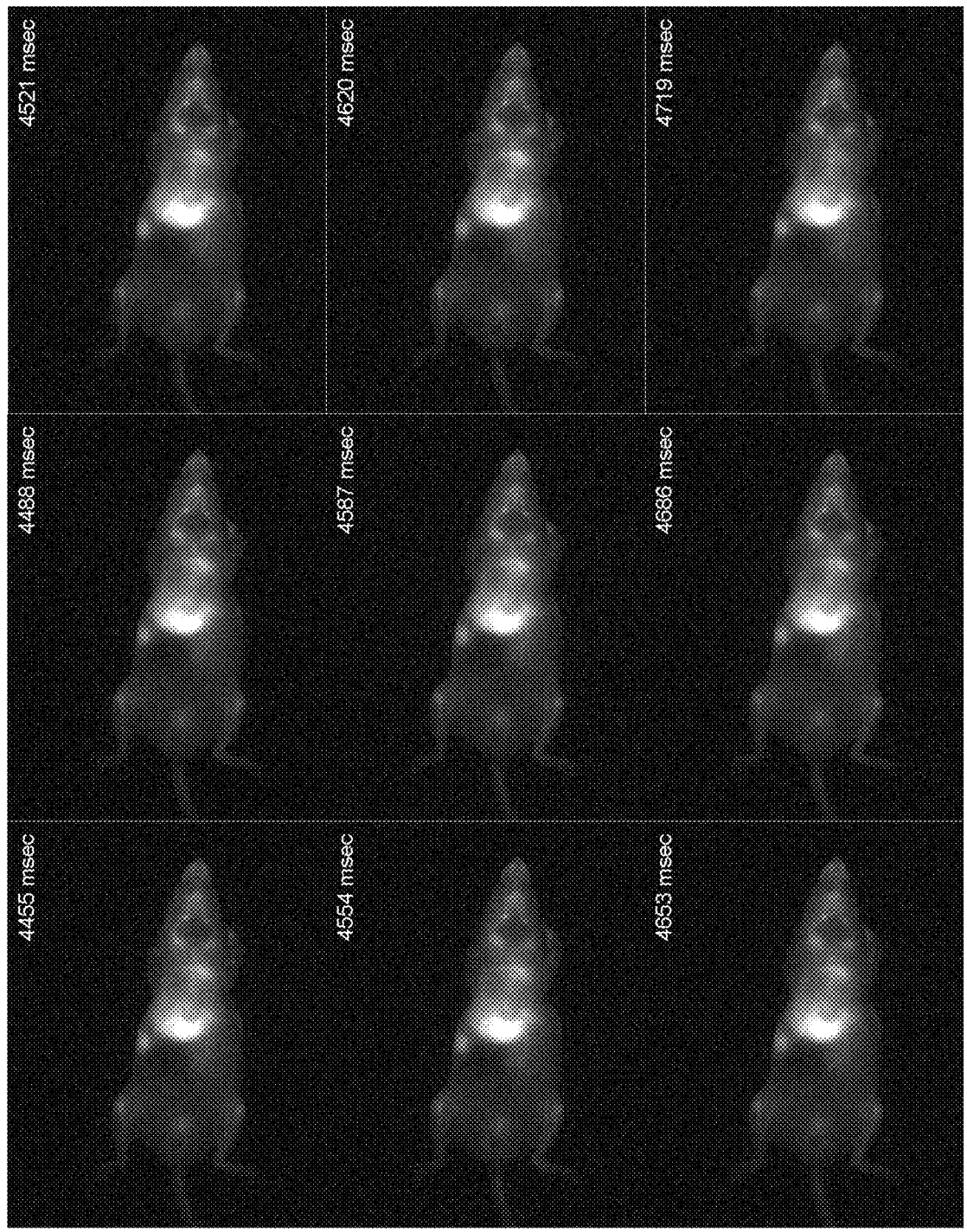
Figure 2:
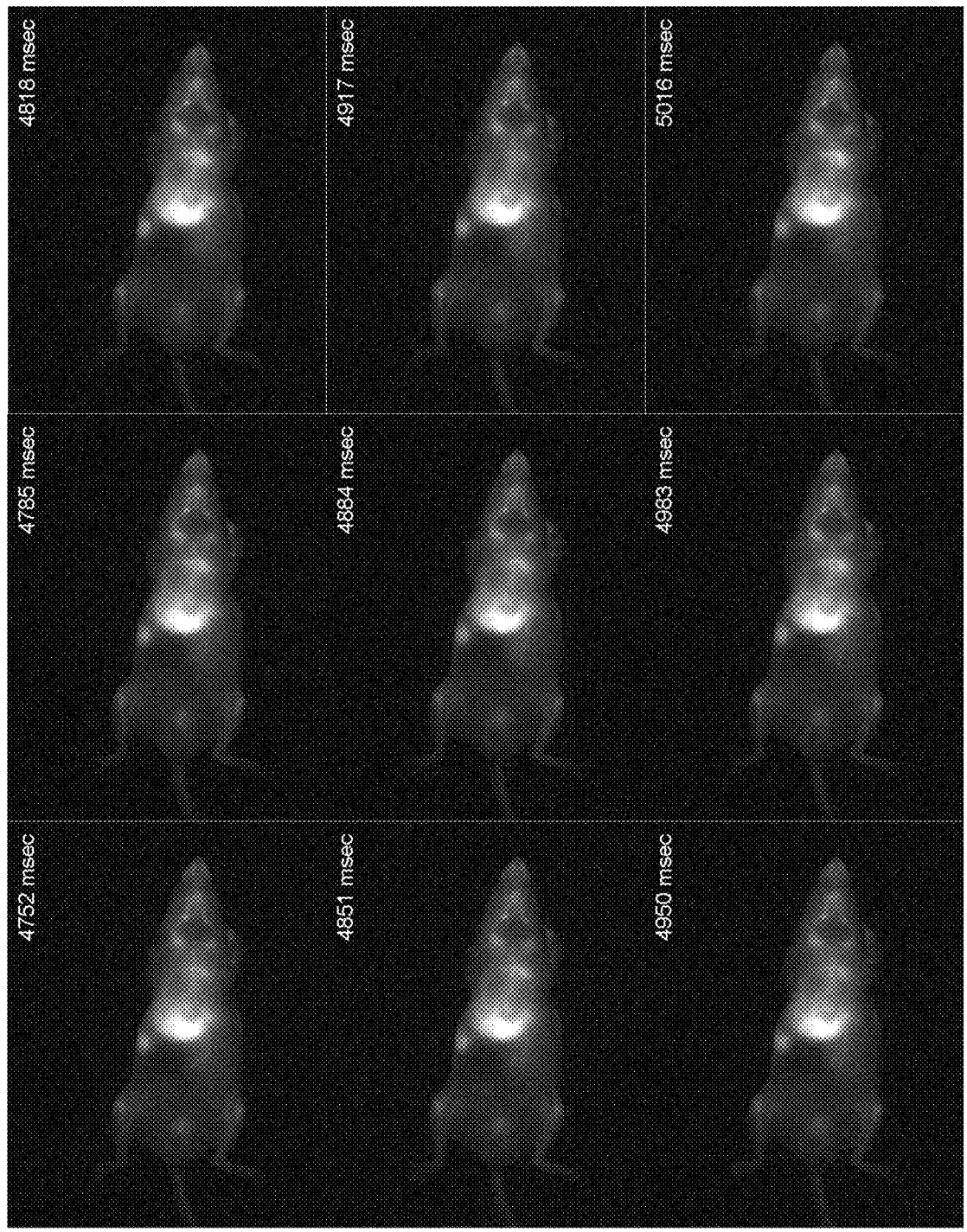
Figure 2:
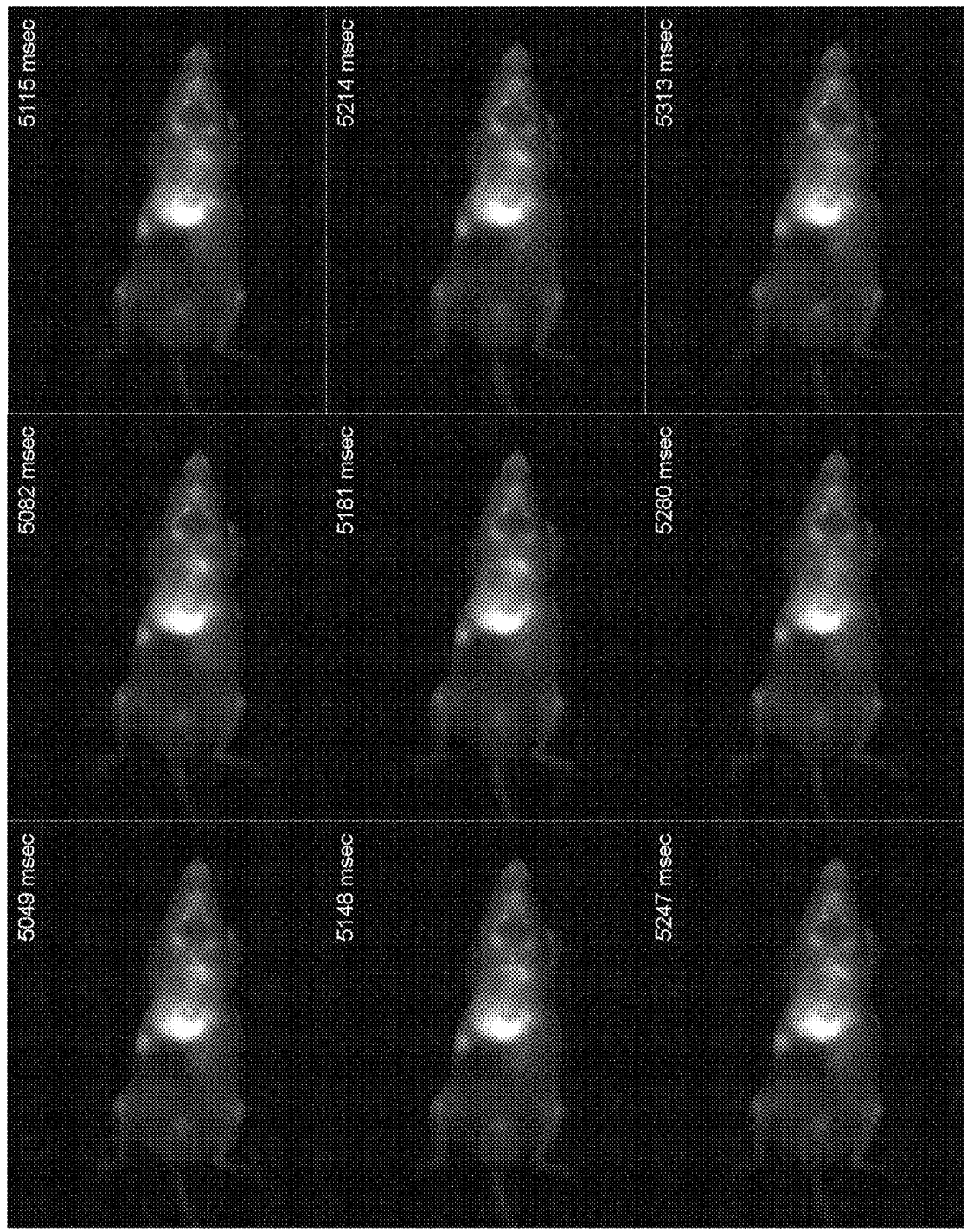
Figure 2:
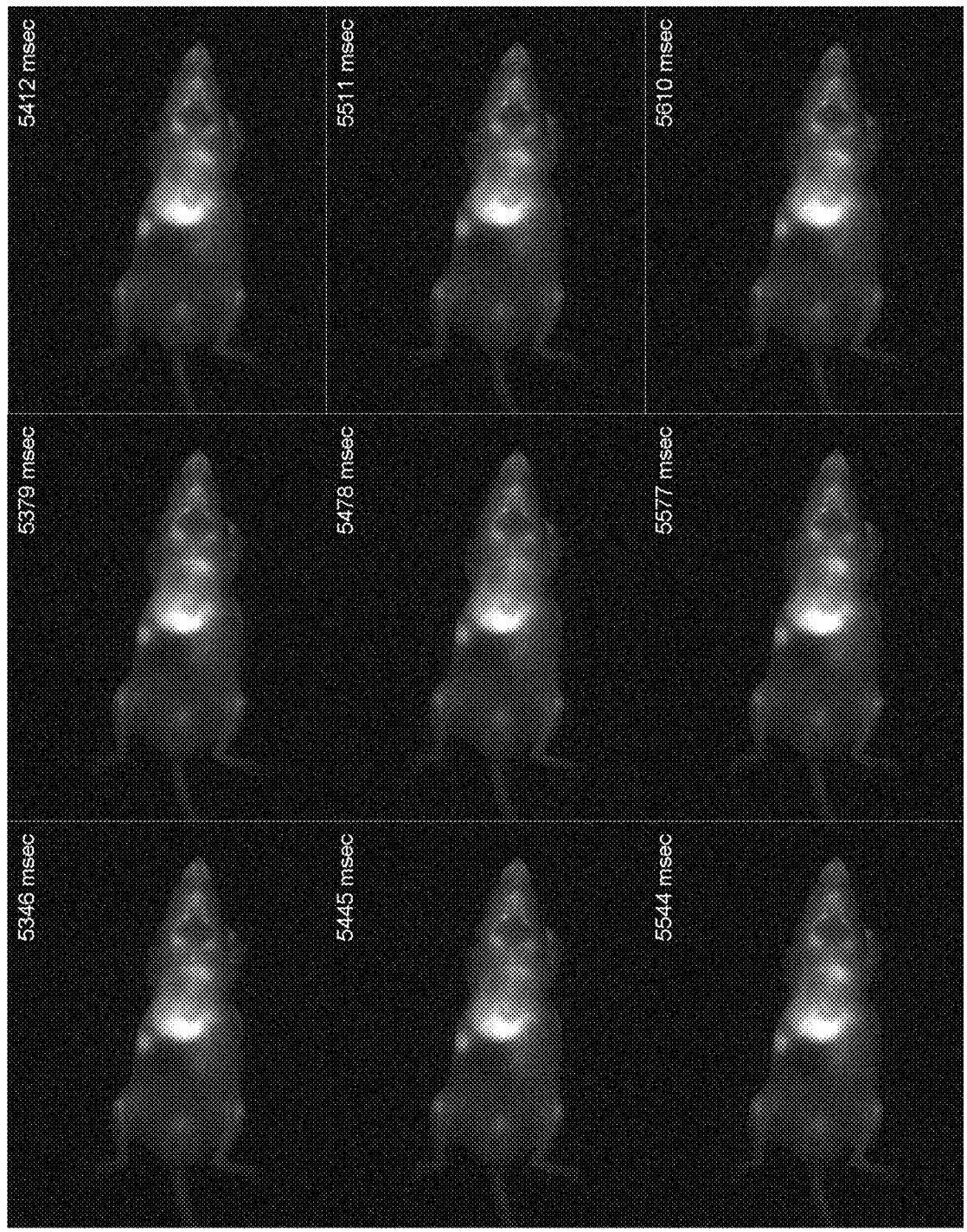
Figure 2:
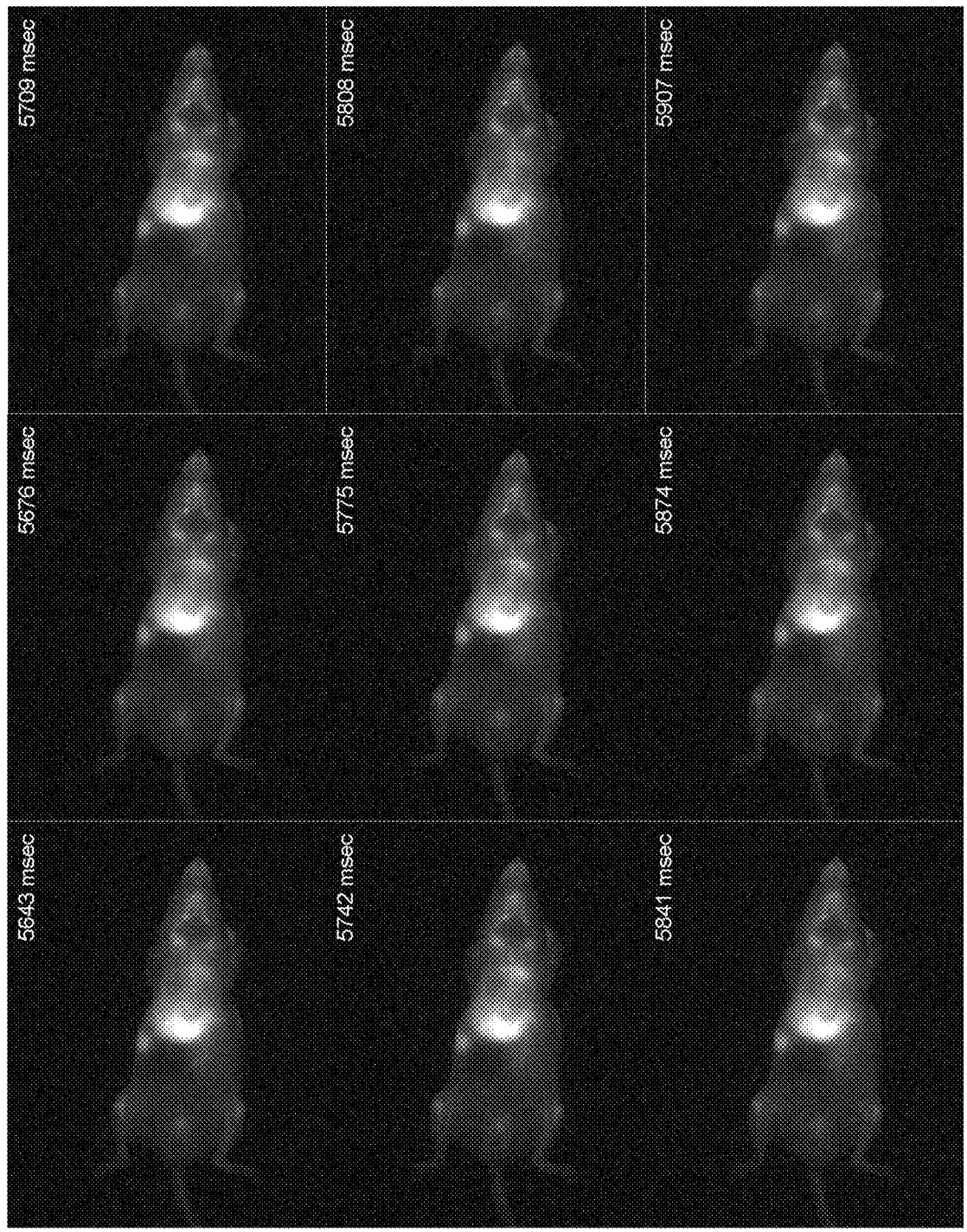

FIG. 2 shows a series of frames taken from a non-invasive SWIR imaging movie. The 808 nm excitation light has a flux of 20 mW/cm$^2$. A 1300 nm longpass filter (Thorlabs) is placed in front of the objective to cut out the excitation light. The InGaAs focal plane (Princeton Instruments, NIRvana, 640×512 pixel) is cooled to −80° C. and runs continuously with 100 ms exposure time and 45 ms read time resulting in ca. 7 fps frame rate.

A nude mouse is anesthetized and placed on its back. The camera and excitation come from the top looking at the front of the mouse. A catheter for injection of the PEG-lipid SWIR Semiconductor nanocrystals is placed in the tail vein. At the beginning of the movie the excitation is already switched on, but the mouse can't be seen. In fact there is absolutely no background/autofluorescence. After a couple of seconds the SWIR Semiconductor nanocrystals are injected and the first signal appearing in the movie. The SWIR semiconductor nanocrystals distribute from the tail to the heart, the lungs, the periphery and finally to the liver sequentially and the signal even shows some saturation effects. This demonstrates that even under sensitive detection settings no background was detected. The heart beat is not fully resolved at this slower frame rate but the breathing motion can be seen on the liver.

The disclosed imaging setup enables a high-speed SWIR imaging. The 808 nm excitation light has a flux of 20 mW/cm². A 1100 nm longpass filter (Thorlabs) is placed in front of the objective to cut out the excitation light. The InGaAs focal plane (Princeton Instruments, NIRvana, 640× 512 pixel) is cooled to −80° C. and runs continuously with 15 ms exposure time and 18 ms read time resulting in ca. 30 fps frame rate. The SWIR semiconductor nanocsrystals are emitting at 1300 nm (QDV). A nude mouse is anesthetized and placed on its back. The camera and excitation come from the top looking at the front of the mouse. A catheter for injection of the PEG-lipid SWIR Semiconductor nanocrystals is placed in the tail vein. The heart beat is now fully resolved at this faster frame rate. The signal change is due to the changes of the blood volume in the heart during the heart cycle.

Figure 3A:
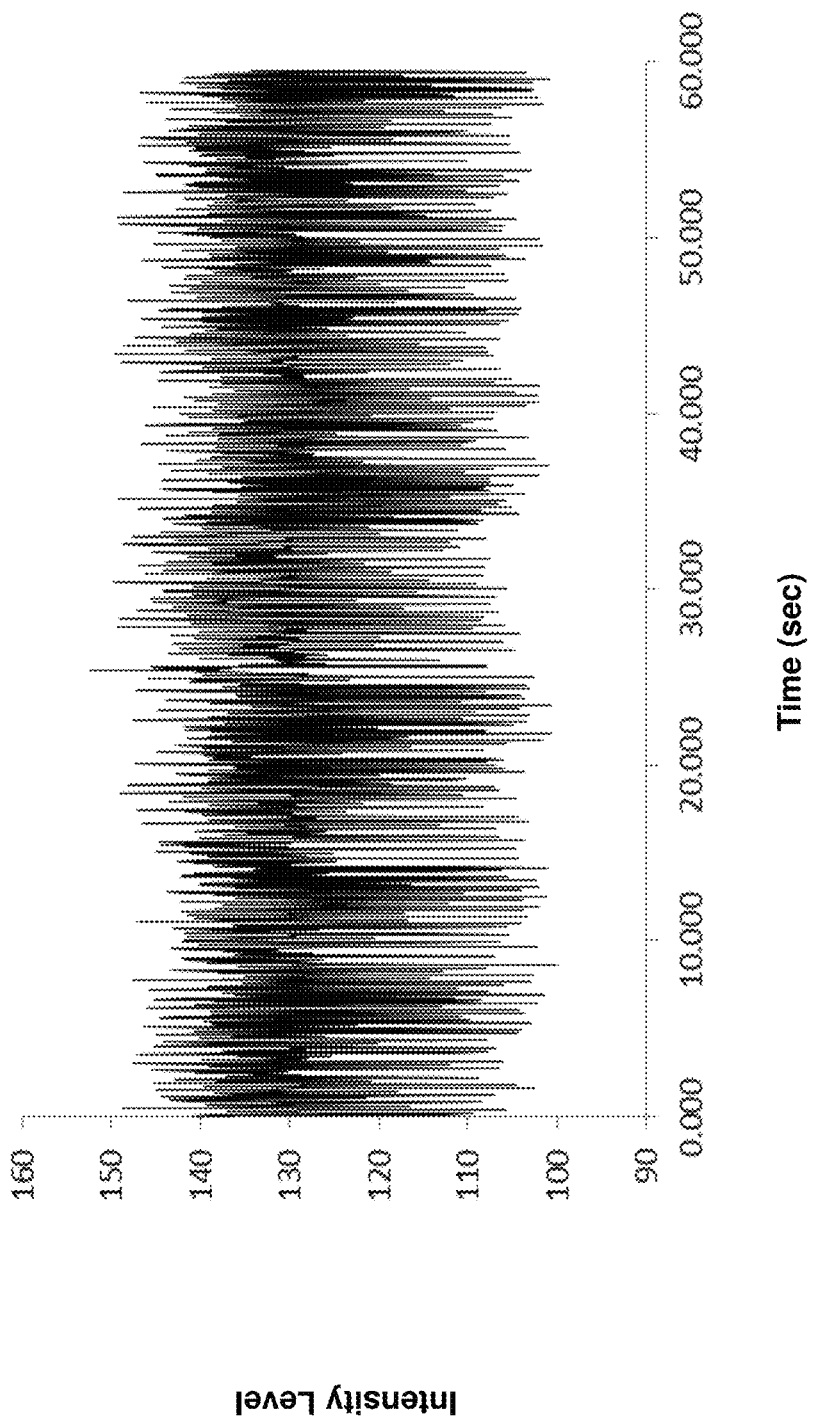
FIGS. 3A-3C depict graphs of a contact-free optical cardiography.
Figure 3B:
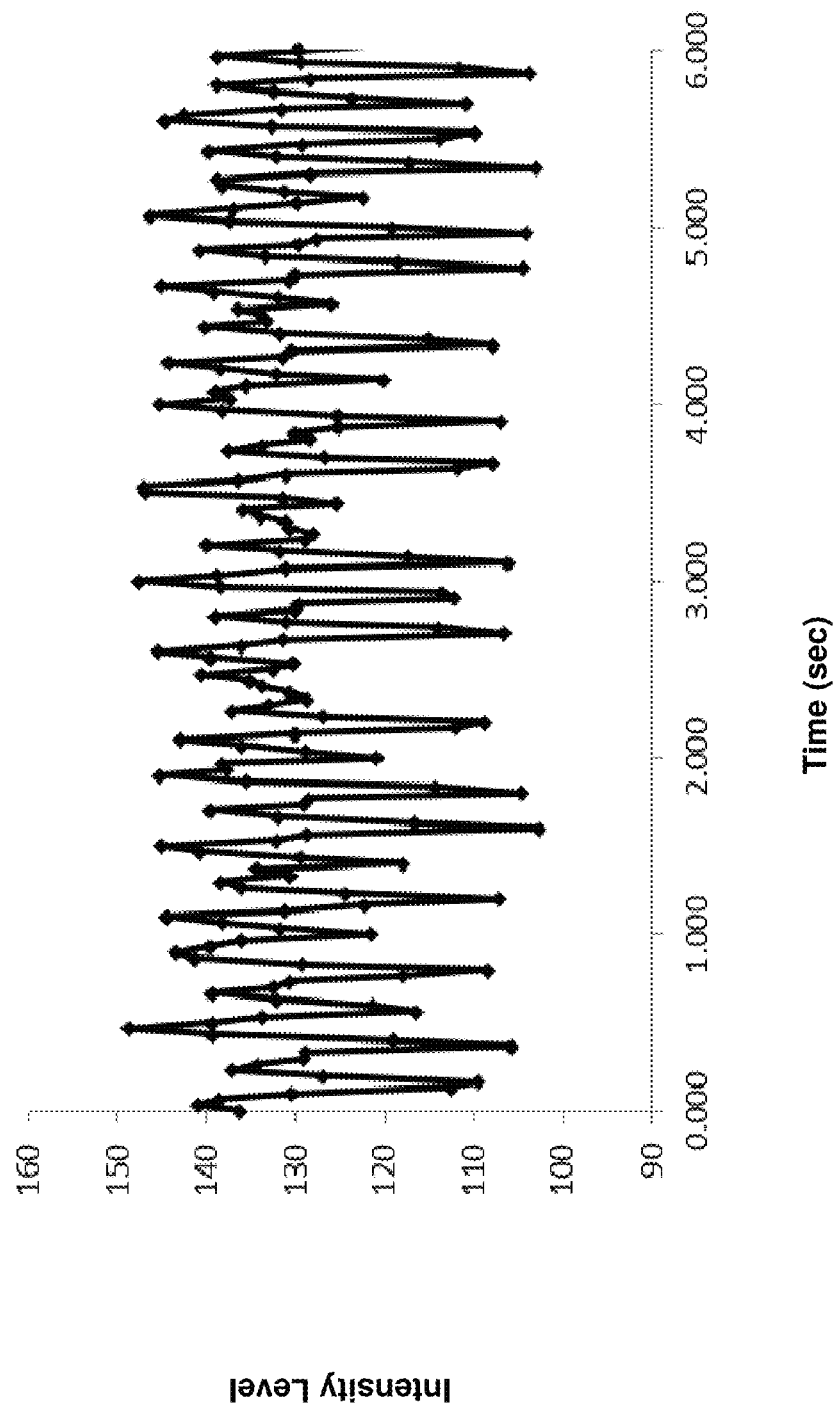
Figure 3C:
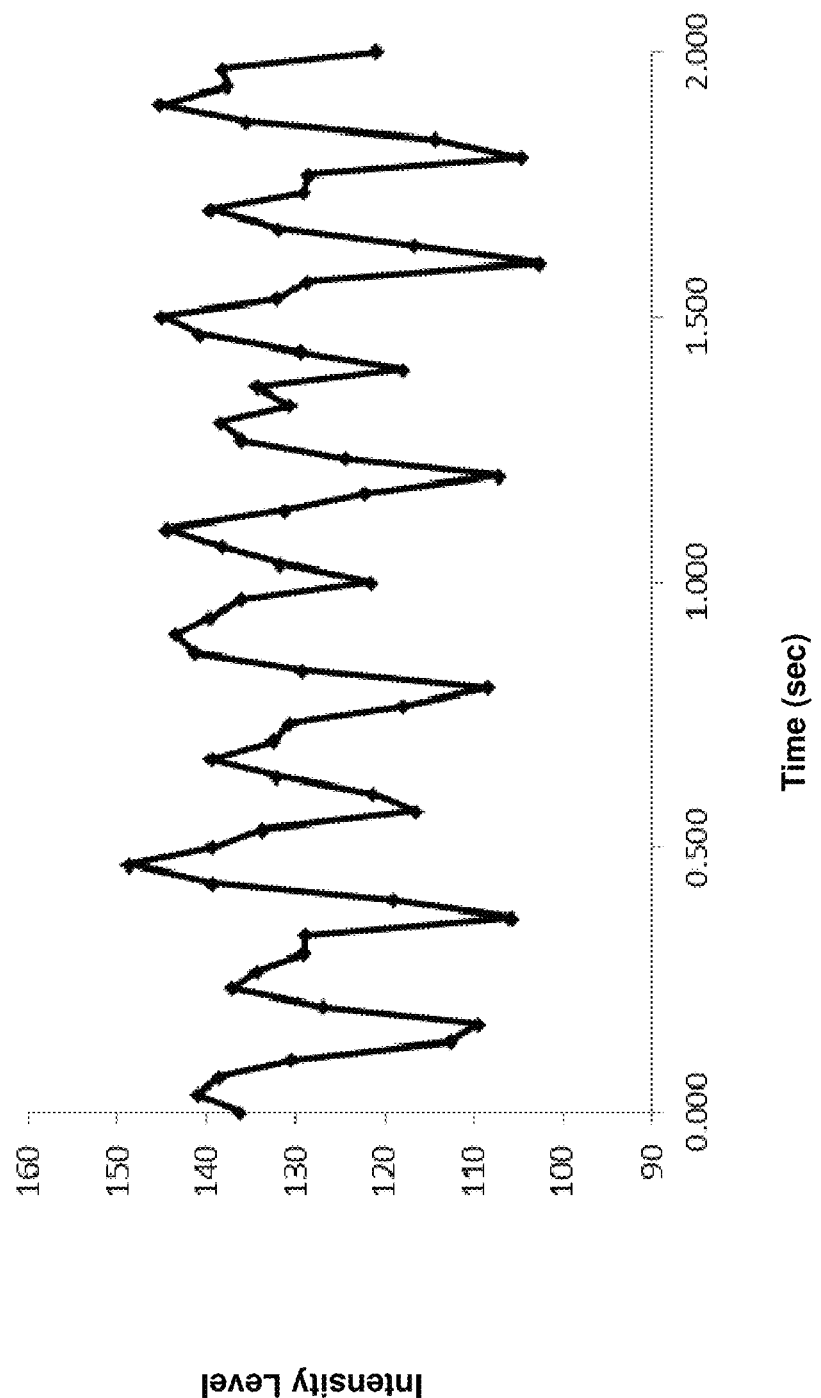

FIGS. 3A-3C show graphs of a contact-free optical cardiography. A region of interest (ROI) is place over the heart in the movie recorded from a high-speed SWIR imaging. The intensity levels are extracted and plotted versus time in seconds. The resolution is lowest in FIG. 3A and the highest FIG. 3C.

This anesthetized mouse from a high-speed SWIR imaging at 30 fps frame rate has 10 beats in 2 sec or 53 beats in 10 sec corresponding to about 320 beats per minute (BPM) or 5 beats per second. Typically, an awake resting mouse has a heart rate of 600-800 BPM or ~10 beats per second 30 frames per second imaging rate would be enough to sample this.

Figure 4A:
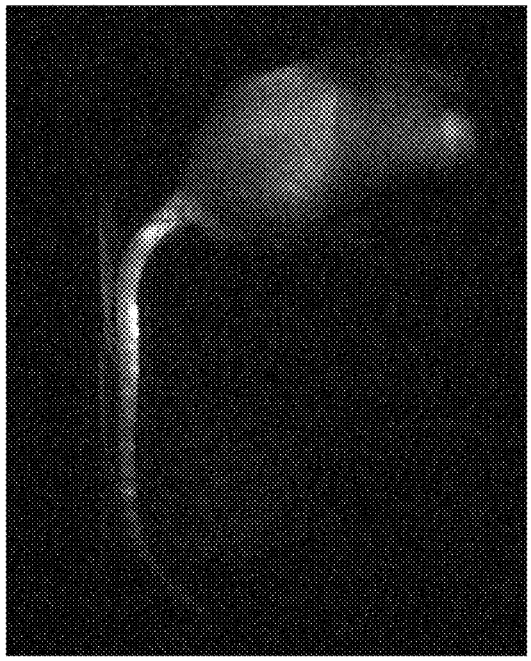
FIGS. 4A-4C depicts a bright SWIR semiconductor nanocrystals imaging of awake mice at various frame rates.
Figure 4B:
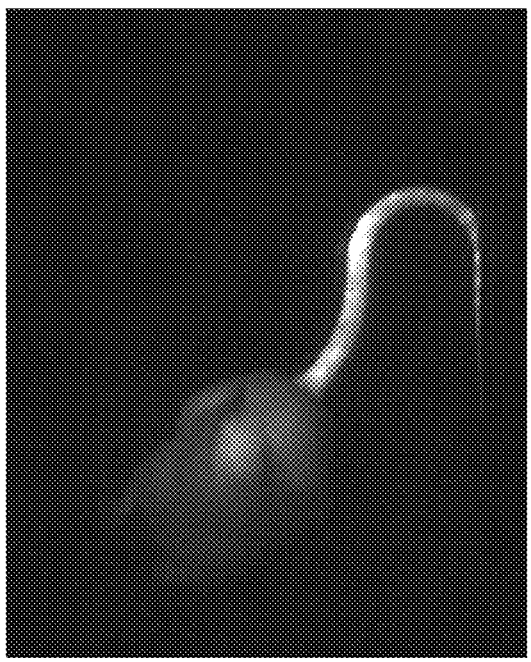
Figure 4C:
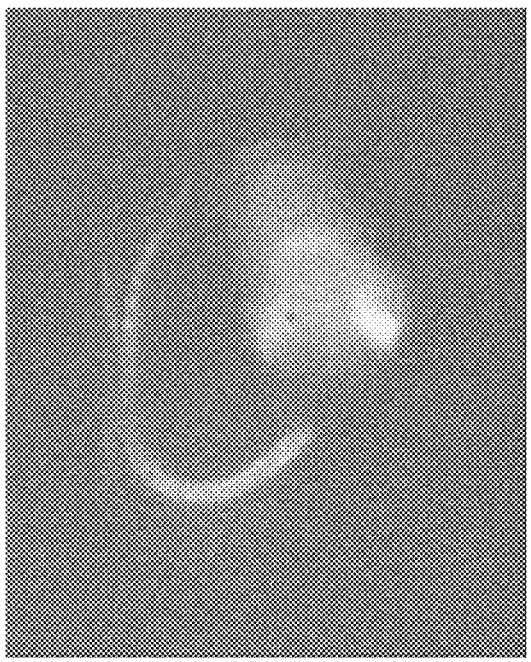
Figure 5:
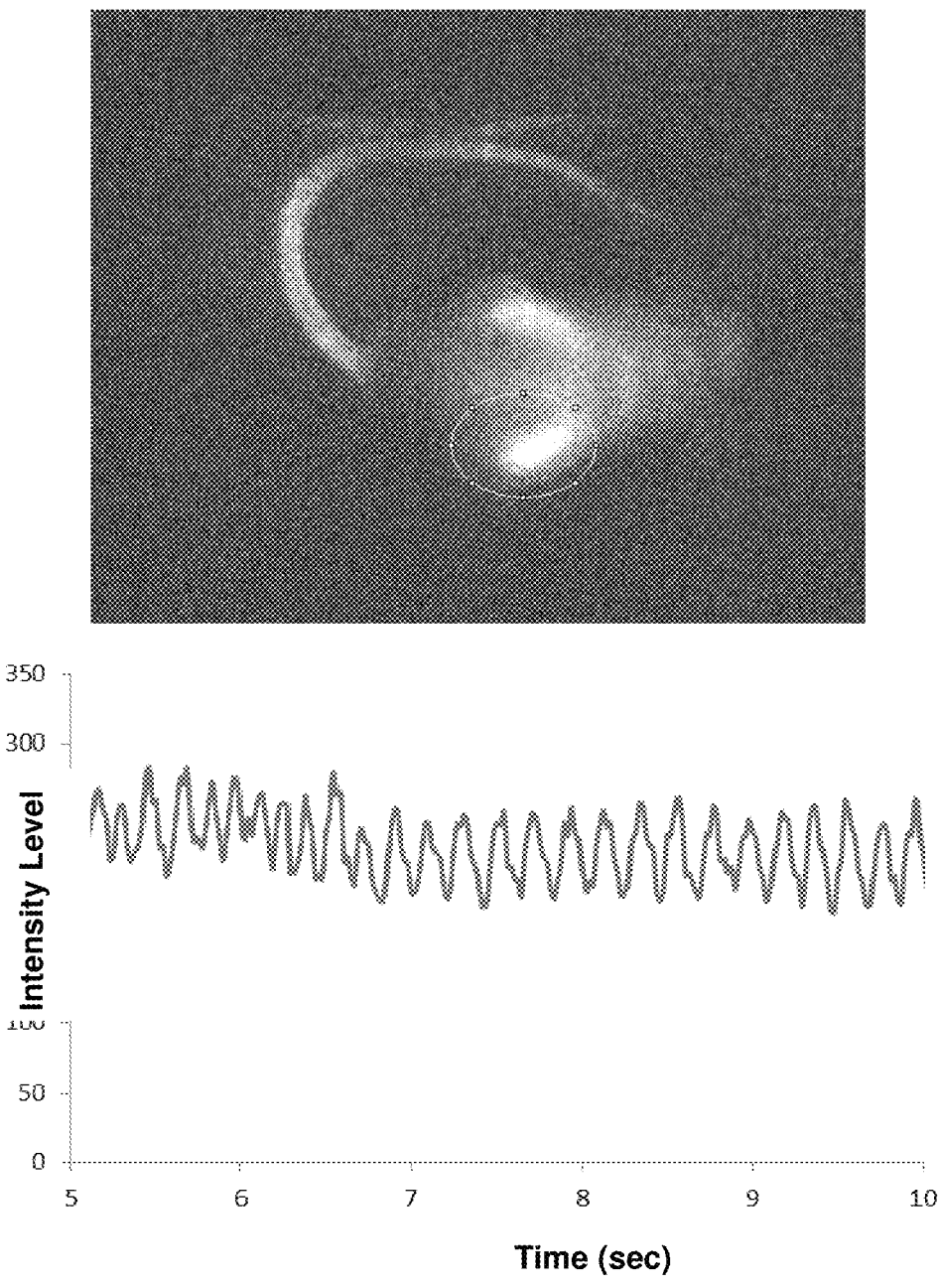
FIG. 5 depicts imaging physiology of awake mice.

FIGS. 4A-4C depicts a representative frame image of a bright SWIR semiconductor nanocrystals imaging of awake mice at various frame rates. The 808 nm excitation light has a flux of 20 mW/cm². A 1100 nm longpass filter (Thorlabs) is placed in front of the objective to cut out the excitation light. The InGaAs focal plane (Princeton Instruments, NIRvana, 640×512 pixel) is cooled to −80° C. and runs continuously with 100 ms exposure time and 9 ms read time resulting in ca. 9 fps frame rate (FIG. 4A), with 25 ms exposure time and 9 ms read time resulting in ca. 29 fps frame rate (FIG. 4B), and with 12 ms exposure time and 9 ms read time resulting in ca. 48 fps frame rate (FIG. 4C). A nude mouse was injected with PEG-lipid SWIR semiconductor nanocrystals emitting at 1300 nm (QDV). The camera and excitation come from the top looking at the front of the mouse. The images show a high signal-to-noise-ratio at 9 fps frame rate, and the movements of the mouse are resolved at this frame rate (FIG. 4A) with no major motion artifacts, but breathing is not resolved yet. The signal-to-noise-ratio is still very high at 29 fps frame rate (FIG. 4B), but breathing is still not resolved at this frame rate. At 48 fps frame rate, signal-to-noise-ratio is still good but not as high as before, but still adequate for a good quality movie (FIG. 4C). At this frame rate the breathing rate of the mouse can be clearly seen due to the movement of the liver within the mouse.

Figure 6:
FIG. 6 depicts a photograph of principle component analysis of FIG. 5.

FIG. 6 shows a bright SWIR semiconductor nanocrystals imaging of physiology in awake mice with a graph of the breathing rate. A region of interest (ROI) is place over the liver and the spleen. The intensity levels are extracted and plotted versus time in seconds.

The disclosed imaging setup enables a spectrally defined SWIR imaging. The 808 nm excitation light has a flux of 50 mW/cm². For spectrally resolved imaging a liquid crystal tunable filter (LCTF) with a 20 nm bandwidth (VariSpec LNIR, Cambridge Research instruments/Perkin Elmer) is mounted in front of the objective. A movie was taken with a miniSWIR imager (Raytheon) at 30 fps. A nude mouse is anesthetized and placed on its back. The camera and excitation come from the top looking at the front of the mouse. A catheter for injection of the PEG-lipid SWIR semiconductor nanocrystals is placed in the tail vein. The first SWIR semiconductor nanocrystals emitting at 1300 nm (QDV) are injected before. As the filter is tuned to 1050 nm the emission of the 1300 nm SWIR semiconductor nanocrystals is not detected anymore. At the beginning of the movie the excitation is already switched on and the first color of SWIR Semiconductor nanocrystals is in the mouse, but the mouse cannot be seen. In fact there is absolutely no background or fluorescence cross talk from the first SWIR semiconductor nanocrystals which is not emitting at 1050 nm. After a couple of seconds, the second SWIR semiconductor nanocrystals emitting at 1050 nm are injected and the first signal is appearing in the movie. The SWIR semiconductor nanocrystals distribute from the tail to the heart, the lungs, the periphery and finally to the liver sequentially. This demonstrates that even with a first color already injected the disclosed setup is not sensitive to crosstalk and can image without background.

FIG. 6 shows a deconvolved image into 5 different channels by principal components analysis with 20 nm bandpass liquid crystal tunable filter (LCTF), at 1050 nm, 30 fps, raytheon imager. The 5 different channels were pseudo color from blue to red and overlaid.

The disclosed imaging setup enables a hyperspectral SWIR imaging with 5 different semiconductor nanocrystals colors with 20 nm bandpass liquid crystal tunable filter (LCTF), 850-1700 nm spectrum. Five different SWIR semiconductor nanocrystals in organic solution in vials are placed in the field of view. For spectrally resolved imaging, a liquid crystal tunable filter (LCTF) with a 20 nm bandwidth (VariSpec LNIR, Cambridge Research instruments/Perkin Elmer) was mounted in front of the objective. It was tuned in 25 nm steps from 850 nm to 1700 nm. Images for each step were with a miniSWIR imager (Raytheon).

Figure 7:
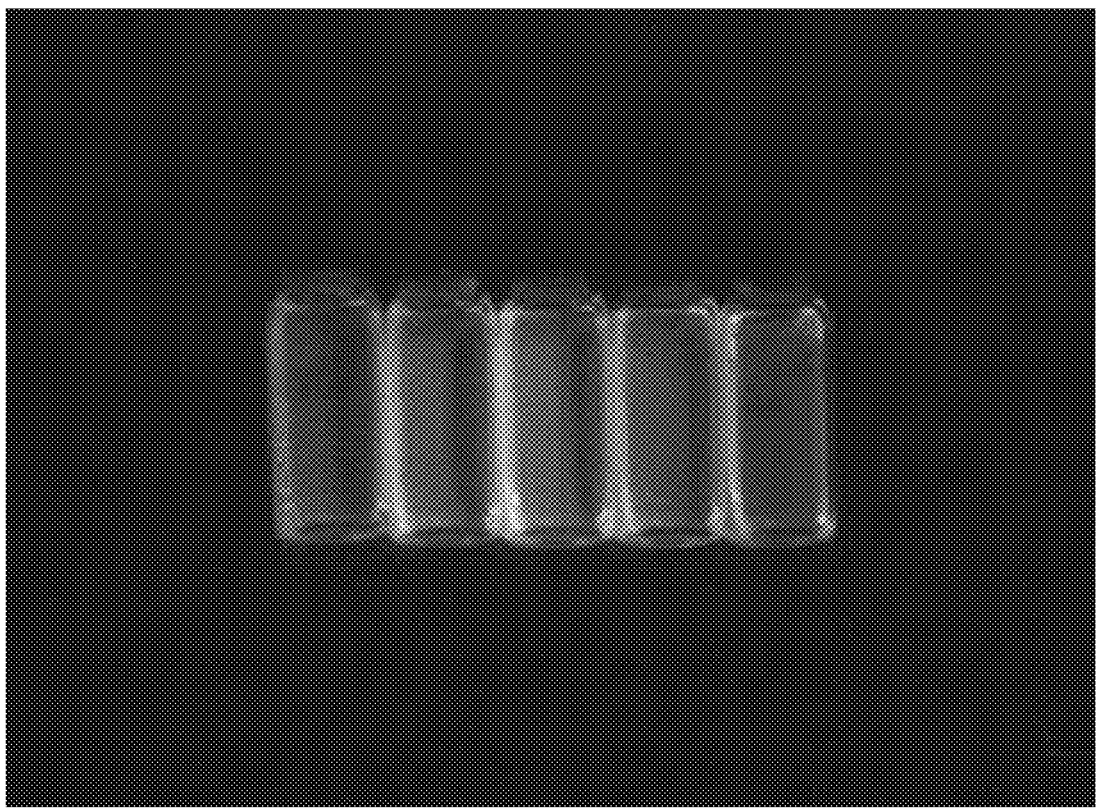
FIG. 7 depicts a photograph of principle component analysis.

FIG. 7 shows a deconvolved image into 5 different channels by principal components analysis with 20 nm bandpass liquid crystal tunable filter (LCTF), at 1050 nm, 30 fps, raytheon imager. The 5 different channels were pseudo color from blue to red and overlaid.

Figure 8:
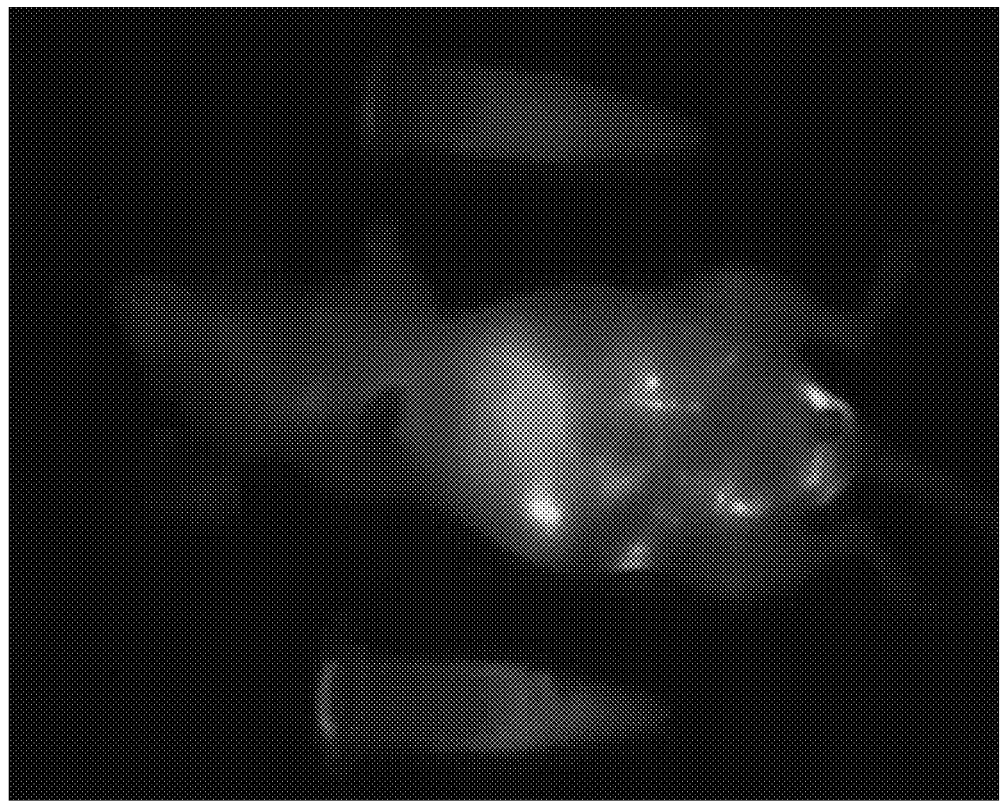
FIG. 8 depicts a color SWIR imaging in vivo.

FIG. 8 shows a color SWIR imaging in vivo. The 808 nm excitation light has a flux of 20 mW/cm². For spectrally resolved imaging, a liquid crystal tunable filter (LCTF) with a 20 nm bandwidth (VariSpec LNIR, Cambridge Research instruments/Perkin Elmer) was mounted in front of the objective. It was tuned in 25 nm steps from 850 nm to 1700 nm. The InGaAs focal plane (Princeton Instruments, NIRvana, 640×512 pixel) is cooled to −80° C. Single frames were recorded for each wavelength step with 1000 ms exposure time. A nude mouse is anesthetized and placed on its back. The camera and excitation come from the top looking at the front of the mouse. One color of SWIR Semiconductor nanocrystals (green) was injected intraperitoneal (ip) and the second color of SWIR Semiconductor nanocrystals (red) was injected intravenously (iv) yielding in different biodistribution pattern in vivo. To vials with diluted particles are placed in the scene as phantoms and for comparison/reference. The hyperspectral image series was deconvolved into 2 different channels by linear unmixing/principal components analysis. The 2 different channels were pseudo color green and red and overlayed.

Figure 9:
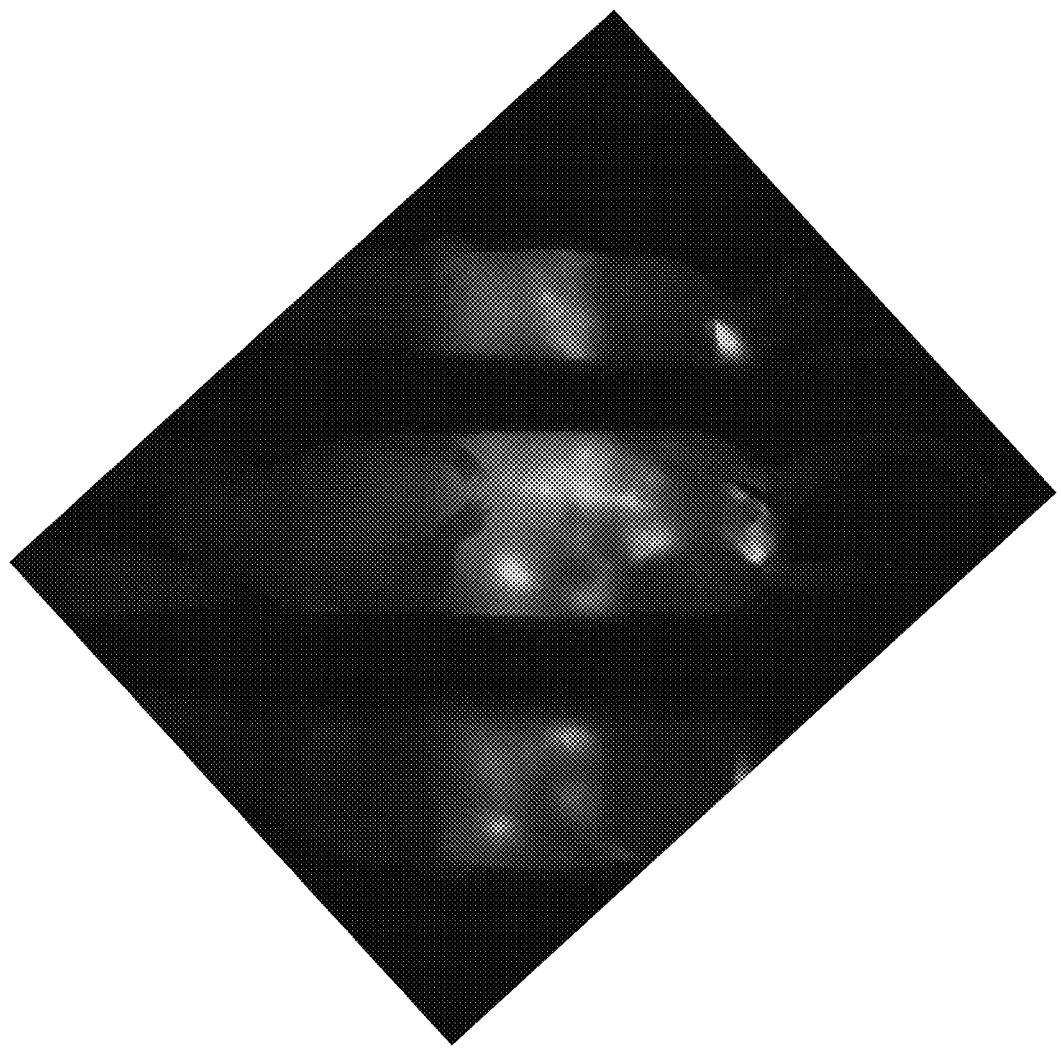
FIG. 9 depicts a color SWIR imaging combined with pseudo-tomography.

FIG. 9 is a color SWIR imaging combined with pseudo-tomography

The 808 nm excitation light has a flux of 20 mW/cm². For spectrally resolved imaging, a liquid crystal tunable filter (LCTF) with a 20 nm bandwidth (VariSpec LNIR, Cambridge Research instruments/Perkin Elmer) was mounted in front of the objective. It was tuned in 25 nm steps from 850 nm to 1700 nm. The InGaAs focal plane (Princeton Instruments, NIRvana, 640×512 pixel) is cooled to −80° C. Single frames were recorded for each wavelength step with 1000 ms exposure time. The nude mouse from FIG. 8 was sacrificed and frozen to be fixated. The camera and excitation come from the top looking at the front of the mouse. Two mirrors are placed next to the object in a 45 degree angle. To vials with diluted particles are placed in the scene as phantoms and for comparison/reference. The hyperspectral image series was deconvolved into 2 different channels by linear unmixing/principal components analysis. The 2 different channels were pseudo color green and red and overlayed.

Figure 10:
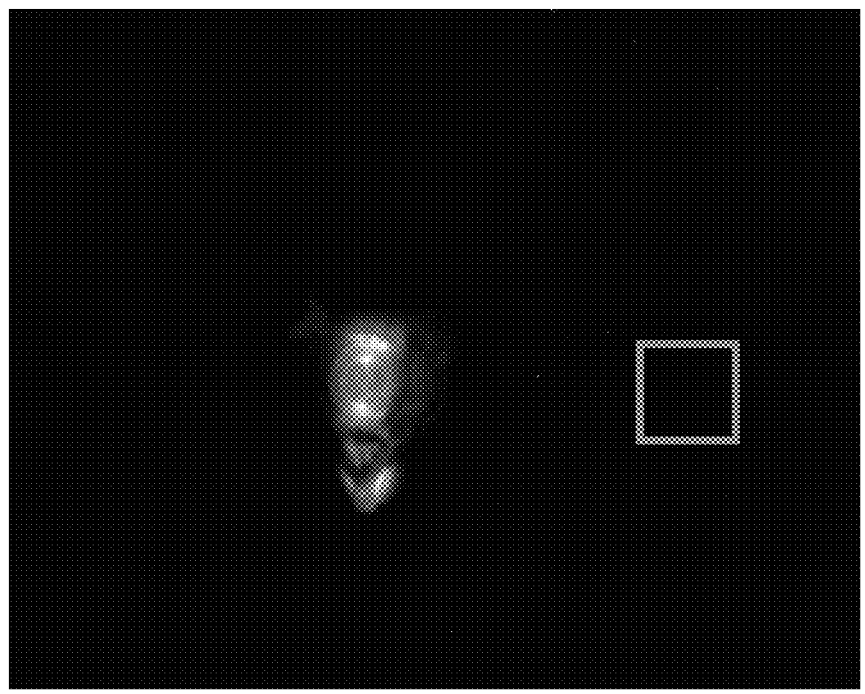
FIG. 10 depicts a window where
Figure 11A:
FIGS. 11A-11D are imaged.
Figure 11B:
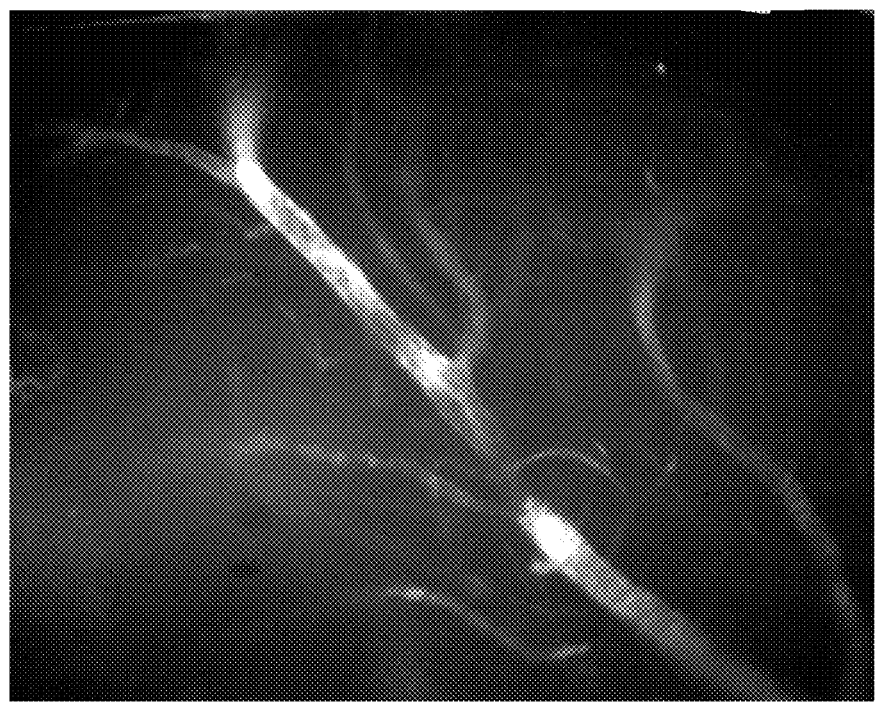
Figure 11C:
Figure 11D:
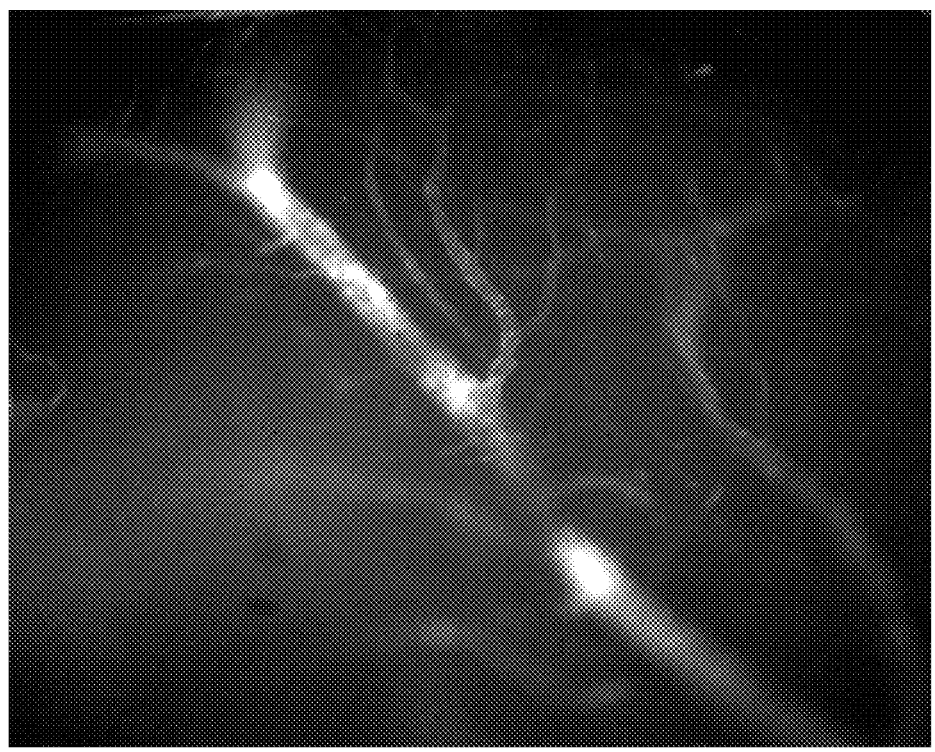

FIGS. 11A-11D shows the OFDI and SWIR correlation. The 808 nm excitation light has a flux of 20 mW/cm$^2$. A 1100 nm longpass filter (Thorlabs) is placed in front of the objective to cut out the excitation light. The InGaAs focal plane (Princeton Instruments, NIRvana, 640×512 pixel) is cooled to −80° C. A mouse with a cranial window was injected with PEG-lipid SWIR semiconductor nanocrystals emitting at 1300 nm (QDV) and sacrificed. The camera and excitation come from the top looking at backside of the head of the mouse. The emission of the SWIR semiconductor nanocrystals can be seen through the window of FIG. 10. Zoom/crop of OFDI pictures of the brain of the same mouse through the cranial window are shown in FIGS. 11A and 11C and SWIR images taken with the disclosed microscope are shown in FIGS. 11C and 11D. Excitation at 850 nm with LED and dichroic and longpass filter to cut out the excitation light were used. SWIR imaging with the disclosed microscope setup at 180 micrometer deep in the brain is demonstrated and the SWIR images are correlated with corresponding OFDI pictures (FIG. 11A with FIG. 11B and FIG. 11C with FIG. 11D, with each pair of photos focused at a different depth).

Figure 12:
FIG. 12 depicts SWIR intravital imaging.
Figure 13A:
FIGS. 13A-13B depict SWIR intravital imaging with high signal intensities (FIG. 13A) and low signal intensities (FIG. 13B)
Figure 13B:
Figure 14:
FIG. 14 depicts SWIR intravital imaging at 25 fps frame rate

FIG. 12 show an SWIR intravital imaging with 17 fps and 850 nm LED excitation light in the microscope setting. Longpass and dichroic filters (Thorlabs) are placed in the setup to cut out the excitation light. The InGaAs focal plane (Princeton Instruments, NIRvana, 640×512 pixel) is cooled to −80° C. and mounted to the sideport of the microscope. A mouse with a cranial window was injected with PEG-lipid SWIR semiconductor nanocrystals emitting at 1300 nm (QDV) and anesthetized and mounted on the microscope. The blood flow in the brain vessels can be imaged at similar depth as 2 photon imaging. But the acquisition rate of the SWIR system is much faster and the contrast and dynamic range is much better. The hemodynamics can be recorded as demonstrated for the blood mixing in the large vessel. FIG. 13A shows an SWIR imaging with high signal intensities, which allows to focus on the blood flow in the major vessels. FIG. 13B shows an SWIR imaging with low signal intensities, which allows to focus on the blood flow and pulsing of the smaller vessels. When the imaging frequency is increased to 25 fps, the different kinetics/arrival times allow to identify arteries and veins in the field of view (FIG. 14).

Figure 15:
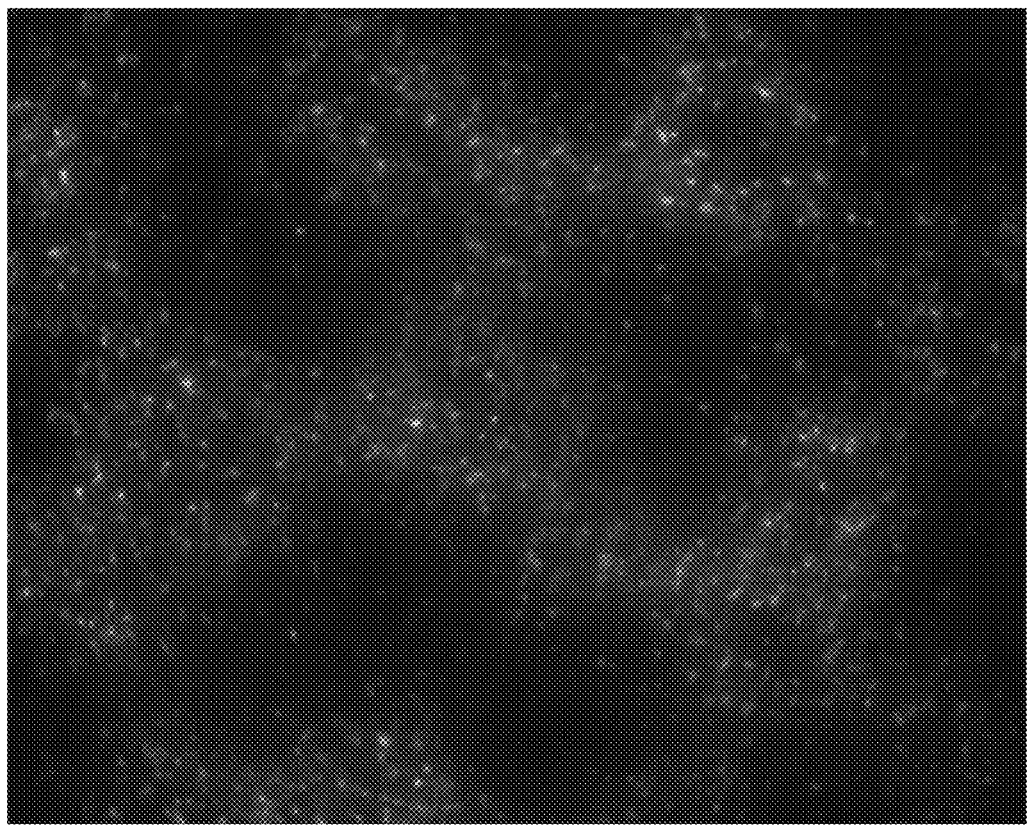
FIG. 15 depicts a photograph of liver microscopy.

FIG. 15 shows a liver microscopy where a mouse was injected with SWIR semiconductor nanocrystals which were taken up by liver macrophages/Kupffer cells. The mouse was perfused and the liver was harvested/excised. The liver was placed on the microscope and z-stack of SWIR images was taken. The Z-Stack was than color coded according to depth (blue shallow, red deep). Single cells/macrophages can be imaged up 150 micrometer depth in this series.

A formulation of semiconductor nanocrystals for SWIR can include a lipid emulsion (lipid droplets in water) with a size distribution ranging from 20 nm to 500 nm. Emulsion can be formulated with 0.7 mg of Phosphatidylcholin, 2.5 mg of 1,2-dioleoyl-sn-glycero-3-phosphoethanolamine-N-[methoxy(polyethylene glycol)-2000]ycol)-2000] (ammonium salt), 40 mg of soybean oil, and 4 mg of SWIR semiconductor nanocrystals. All components were mixed in chloroform. The solvent was evaporated to form a lipid film. 2 ml of 0.9% NaCl was added to the film and sonicated to form an emulsion. This emulsion was filtered before the injection through a 0.45 um filter.

The formulation can include PEGylated phospholipids which cause a long circulation time in vivo/in the mouse. After injection the larger particles in this formulation can be detected/imaged as distinct events and therefore allow tracking of the blood flow in SWIR microscope setting. The particles can be small enough to be only detected in focus when imaged, as soon as they move out of focus their image can get blurred and their signal can become indistinguishable form the background. This can be used to generate three dimensional data sets with traces of the particles representing the blood flow in this volume.

A movie/stack with e.g. 100 to 1000 frames at each depth can be acquired. The average intensity for each pixel over all collected frames can be calculated. This average is subtracted from each pixel in each frame to generate a difference movie/stack. This represents/isolates only the dynamic information in the focus of the image, all dynamic information from out-of-focus particles is blurred, and therefor indistinguishable from the constant non-dynamic background which is subtracted.

A maximum intensity projection of difference movie/ stack shows the particles traces and gives an outline of flow distribution in the vascular network of the imaged tissue (e.g. liver or brain). Only flow traces from particles in focus in the image show up, but not from particles which are out of focus. Therefor the generated three-dimensional data set has a high z-resolution, which is different to a normal wide field microscope picture. This can be used to achieve axial sectioning similar to confocal and multiphoton imaging.

Furthermore the difference movie/stack can be used to calculate the distribution of the blood flow, either by single particle tracking approaches or a technique called particle image velocimetry (PIV). These techniques generate vector fields representing the blood flow in the imaged volume/ tissue.

In addition to the maximum intensity projection, it is possible to replace the value of each pixel (which is the positive or negative deviation from the mean) by the absolute value. The sum and the average of all frames of the stack now show the vessels in way which is comparable to a multiphoton image.

Due to the long wavelengths (e.g. 808 nm excitation, ca. 1200 nm emission) of SWIR imaging, imaging depth of 200-300 micrometer in brain tissue of a living mouse which is similar to multiphoton imaging exciting at 810 nm can be achieved.

With this approach generate three dimensional "flow maps" of large tissue volumes can be generated. It can be done in a much shorter time than multiphoton imaging approaches and with a much deeper penetration depth compared to confocal microscopy in the visible and near infrared region (400 nm to 1000 nm) of the optical spectrum.

Figure 16:
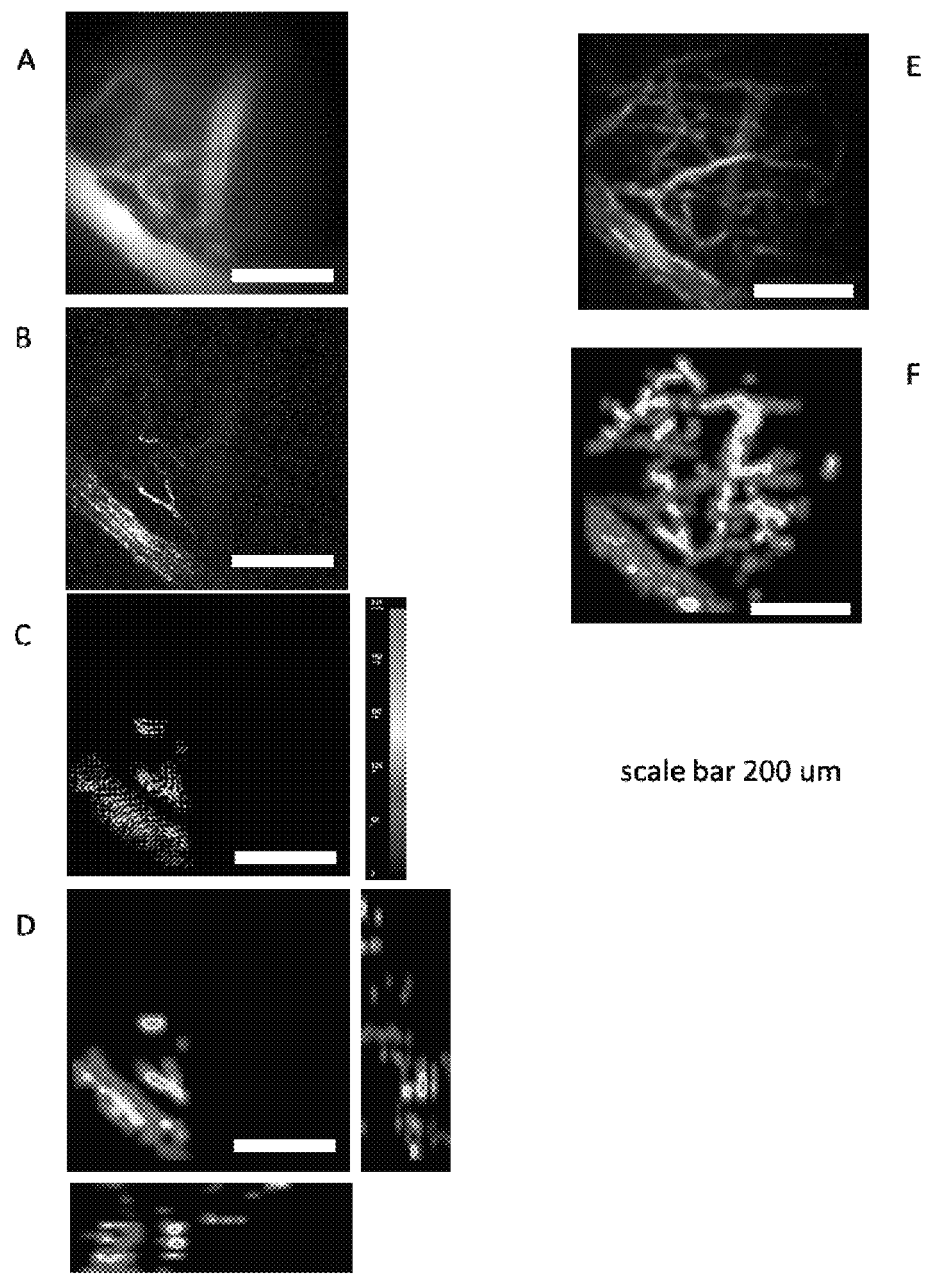
FIG. 16 depicts high-speed semiconductor nanocrystal-SWIR intravital microscopy for deep tissue imaging and blood flow measurement from wide field SWIR data to 3D flow map of brain tissue.

FIG. 16 shows high-speed semiconductor nanocrystal-SWIR intravital microscopy for deep tissue imaging and blood flow measurement from wide field SWIR data to 3D flow map of brain tissue. The images are SWIR images of brain in a mouse with a cranial window. FIG. 16(A) shows average of 100 frames taken as a movie. FIG. 16(B) shows maximum intensity projection of difference stack (subtracted average (A)), which shows only particles in focus (Z-sectioning). FIG. 16(C) shows vector map of flow distribution generated by particle image velocimetry (PIV) of difference stack (subtracted average (A)) with scale bar for velocities (um/s). FIG. 16(D) shows magnitude map corresponding to vector map in (C) with orthogonal sections showing also the other slices of the 3D stack. FIG. 16(E) shows maximum intensity projection of all Z-slice like the one shown in (B) (150 um thick Z-Stack). Corresponding maximum intensity projection of 3D magnitude flow map was generated through PIV.

Figure 17:
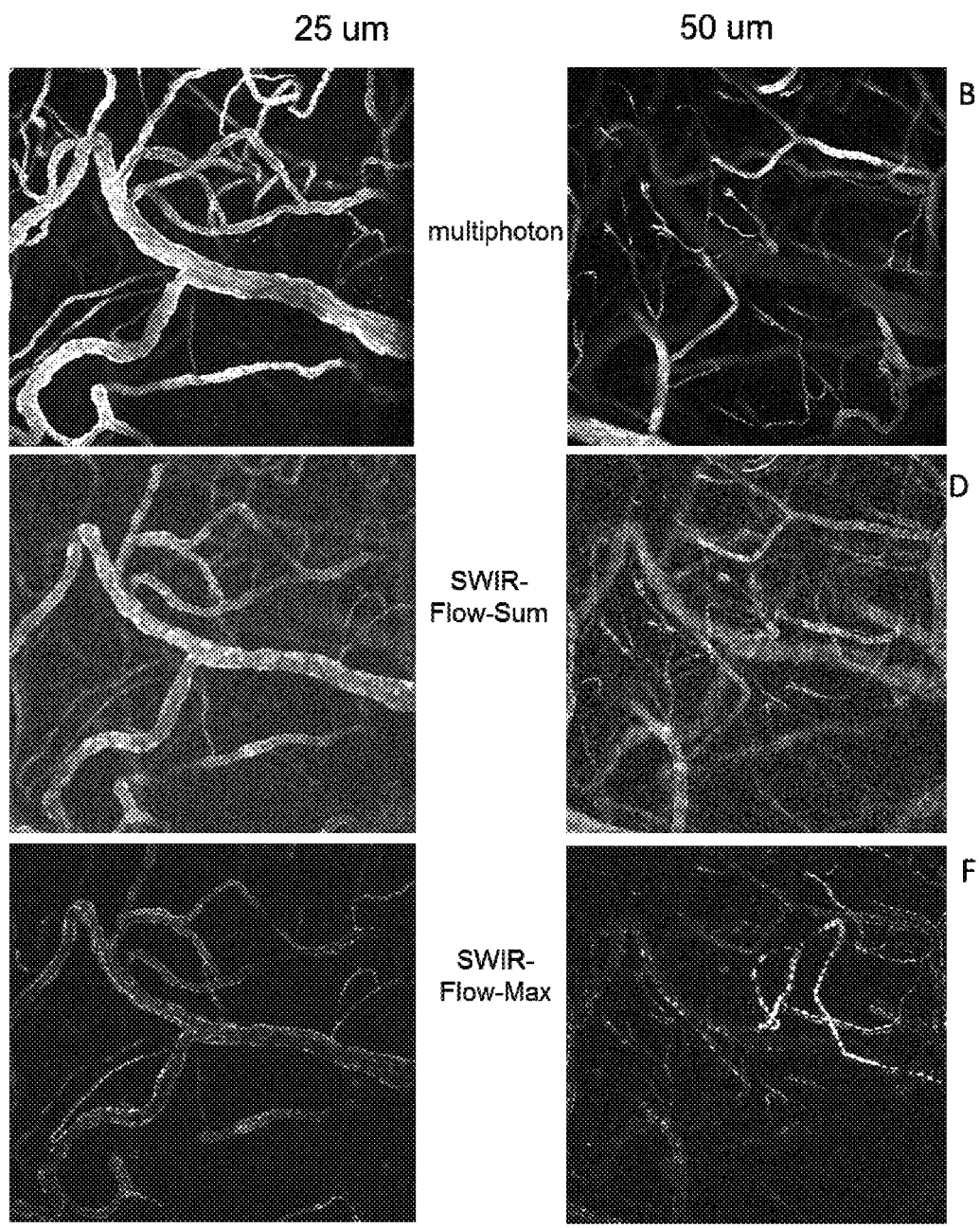
FIG. 17 depicts high-speed semiconductor nanocrystal-SWIR intravital microscopy for deep tissue imaging and blood flow measurement with comparison between Multiphoton and SWIR.

FIG. 17 shows high-speed semiconductor nanocrystal-SWIR intravital microscopy for deep tissue imaging and blood flow measurement. Multiphoton and SWIR were compared. FIG. 17(A) and FIG. 17(B) show Multiphoton images of brain in a mouse with a cranial window at 25 um and 50 um. FIG. 17(C) and FIG. 17(D) show corresponding SWIR images generated as a sum of absolute values of the difference stack (subtracted the average) at 25 um and 50 um. FIG. 17(E) and FIG. 17(F) show corresponding SWIR images generated as a maximum intensity projection of the difference stack (subtracted the average) at 25 um and 50 um.

Figure 18:
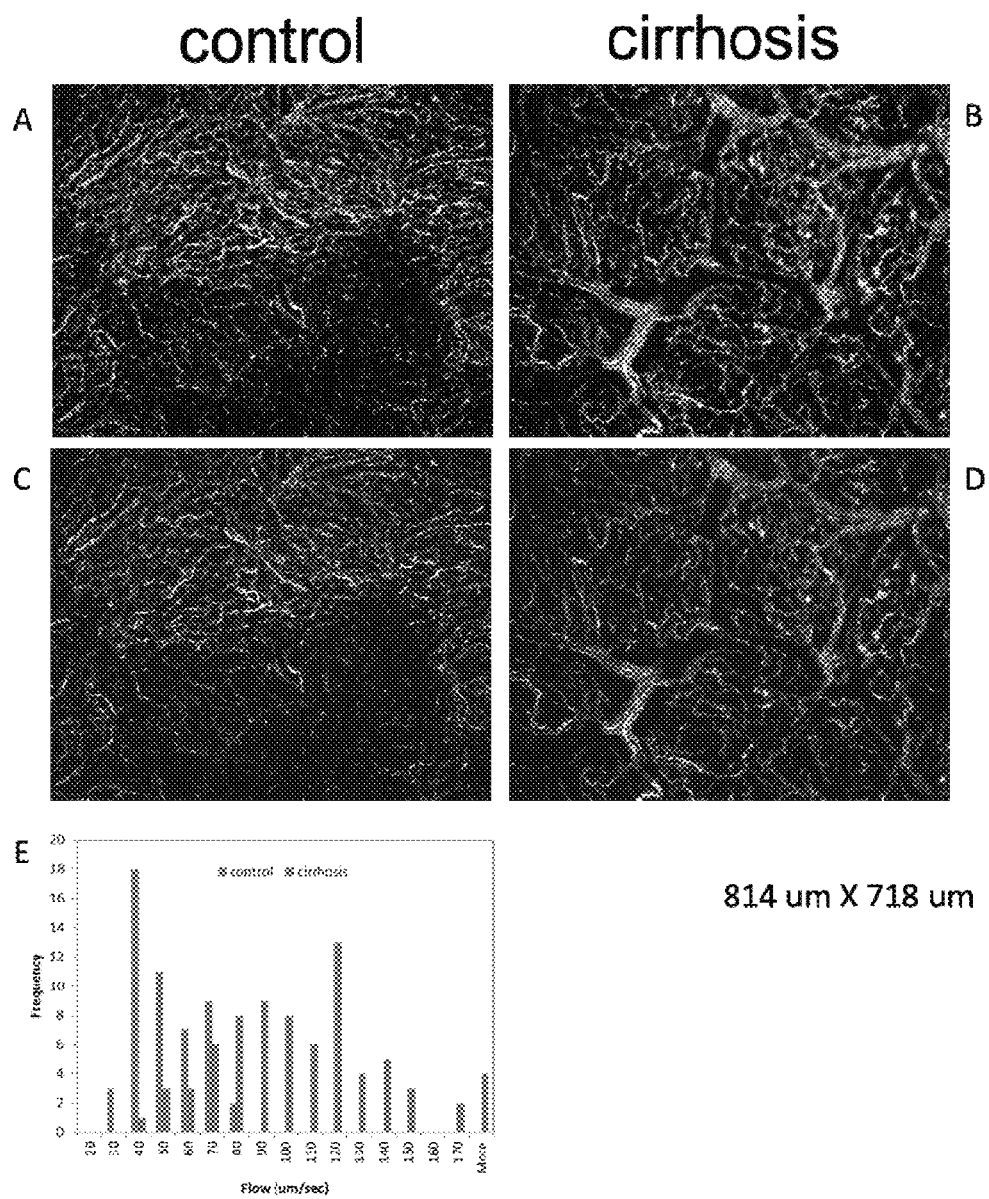
FIG. 18 depicts high-speed semiconductor nanocrystal-SWIR intravital microscopy for deep tissue imaging and blood flow measurement.

FIG. 18 shows high-speed semiconductor nanocrystal-SWIR intravital microscopy for deep tissue imaging and blood flow measurement. FIG. 18(A) and FIG. 18(C) show maximum intensity projection of particle traces of 120 um deep Z-stack recorded in vivo of the liver of a control mouse. FIG. 18(B) and FIG. 18(D) show maximum intensity projection of particle traces of 120 um deep Z-stack recorded in vivo of the liver of a cirrhotic mouse. FIG. 18(E) shows histogram of flow distribution in sinusoidal capillaries of a control/healthy and a cirrhotic mouse. The average flow speed in the healthy mouse is 47+/−13 um/sec and 105+/−42 um/sec in the cirrhotic mouse.

Figure 19:
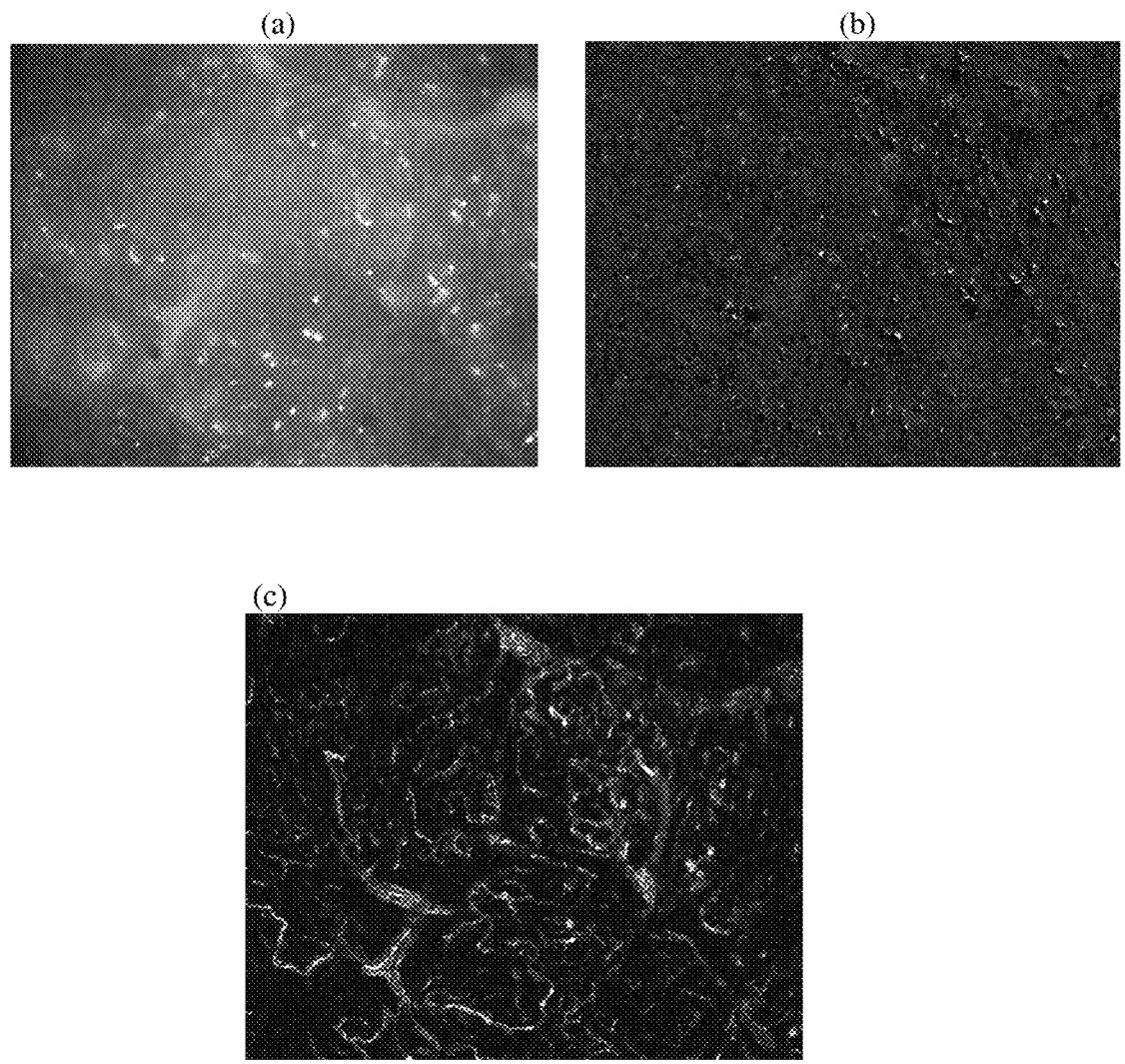
FIG. 19 depicts five steps to 3D flow map.
Figure 19:
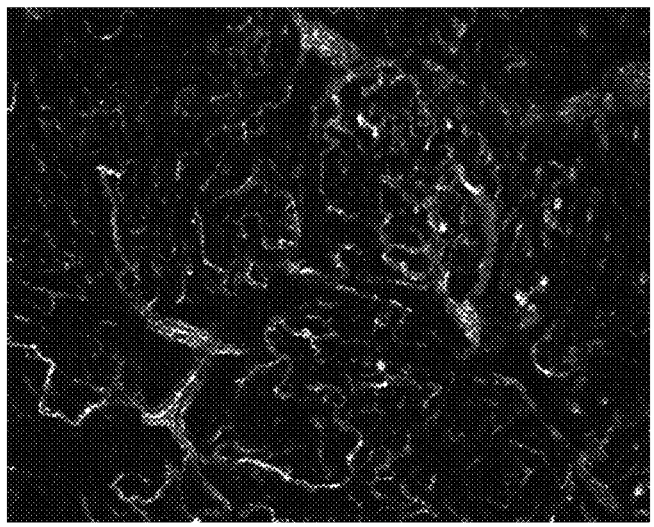
Figure 19:
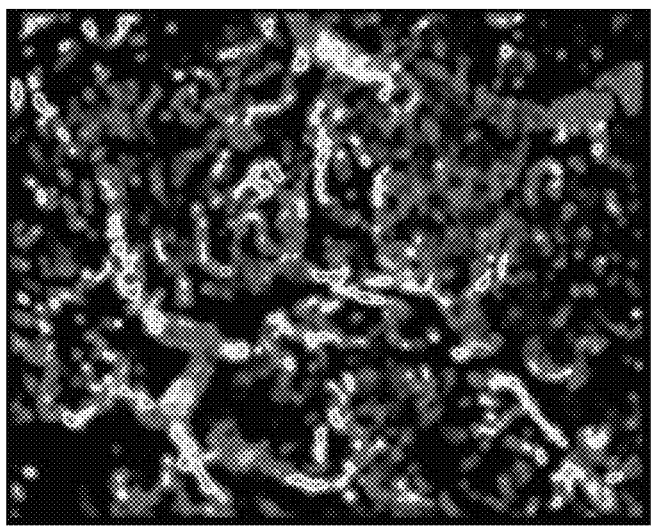
Figure 19:
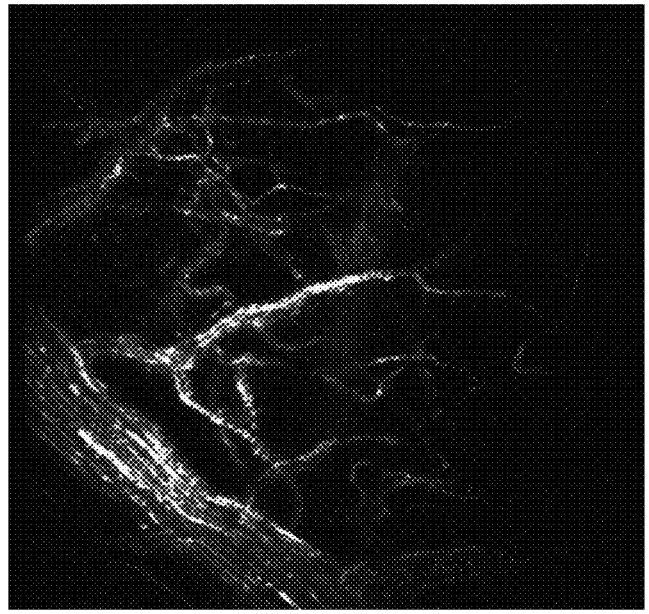
Figure 19:
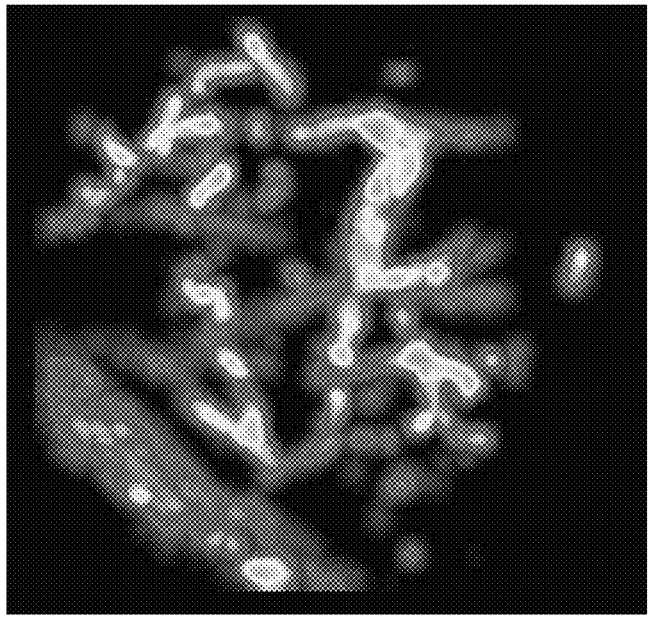

FIG. 19 shows five steps to 3D flow map. Step 1 is raw data acquisition for 10 seconds (FIG. 19(a)). Step 2 subtracts average (FIG. 19(b)). Step 3 is maximum intensity projection (FIG. 19(c)). Step 4 is Particle Image Velocimetry (PIV) (FIG. 19(d) and FIG. 19(e)); FIG. 19(d) shows maximum intensity projection, and FIG. 19(e) shows Particle Image Velocimetry (PIV). FIG. 19(d) and FIG. 19(e) show cirrhotic liver. Step 5 repeats for each Z-step (total 5 min/300 um) (FIG. 19(f) and FIG. 19(g)); FIG. 19(f) shows maximum intensity projection 3D Stack, and FIG. 19(g) shows PIV 3D Stack. FIG. 19(f) and FIG. 19(g) show brain tissue.

Other embodiments are within the scope of the following claims.

What is claimed is:

1. A method of imaging comprising:
introducing a composition including a particle containing a semiconductor nanocrystal comprising indium arsenide into a subject, wherein the semiconductor nanocrystal includes a core and an outer layer including a solubilizing ligand wherein the ligand includes a first monomer unit including a first moiety having affinity for a surface of the nanocrystal, a second monomer unit including a second moiety having a high water solubility including a polyethylene glycol, wherein a hydrodynamic diameter of the semiconductor nanocrystal is less than 30 nm and the semiconductor nanocrystal emits light having a wavelength greater than 900 nm;
a third monomer unit including a third moiety having a selectively reactive functional group or a selectively binding functional group;
exciting the particle with an excitation light source;
detecting emission from the particle in short wavelength infrared (SWIR) spectrum including sampling at an imaging frequency of at least 48 fps over a range from 950 nm to 1700 nm; and
generating a real-time image of an area surrounding of the subject from the detected SWIR emission.

2. The method of claim 1, wherein excitation spectrum is tunable.

3. The method of claim 1, wherein the detecting the emission includes sampling at an imaging frequency of at least 6 fps.

4. The method of claim 1, wherein the nanocrystal includes a core of a first semiconductor material and an overcoating of a second semiconductor material on the core wherein the first semiconductor material and the second semiconductor material are selected so that, upon excitation, one carrier is substantially confined to the core and the other carrier is substantially confined to the overcoating.

5. The method of claim 1, wherein a material of the semiconductor nanocrystal is InAs.

6. The method of claim 1, wherein the semiconductor nanocrystal emits light having a wavelength greater than 1200 nm.

7. An imaging apparatus comprising:
a source of excitation light configured to direct the excitation light at a subject stage;
a detector configured to collect emitted light from a subject on the subject stage, wherein the emitted light is in a short wavelength infrared (SWIR) wavelength region from a semiconductor nanocrystal comprising indium arsenide by sampling at an imaging frequency of at least 48 fps over a range from 950 nm to 1700 nm; and
an image generator configured to create a real-time image from the detected emitted light, wherein the semiconductor nanocrystal includes a core and an outer layer including a solubilizing ligand wherein the ligand includes a first monomer unit including a first moiety having affinity for a surface of the nanocrystal, a second monomer unit including a second moiety having a high water solubility including a polyethylene glycol, wherein a hydrodynamic diameter of the semiconductor nanocrystal is less than 30 nm and the semiconductor nanocrystal emits light having a wavelength greater than 900 nm, and a third monomer unit including a third moiety having a selectively reactive functional group or a selectively binding functional group.

8. The imaging apparatus of claim 7, wherein the detector samples at a frame rate at least 6 fps.

9. The imaging apparatus of claim 7, wherein the emitted light from the semiconductor nanocrystal has a quantum yield of at least 1%.

10. The imaging apparatus of claim 7, wherein the emitted light from the semiconductor nanocrystal has a quantum yield of at least 30%.

11. The method of claim 1, wherein a quantum yield of the semiconductor nanocrystal is at least 30%.

12. The imaging apparatus of claim 7, wherein a quantum yield of the semiconductor nanocrystal is at least 30%.

13. The method of claim 1, wherein the second moiety is a poly(alkylene oxide) moiety.

* * * * *